United States Patent
Crawford et al.

[11] Patent Number: 6,077,812
[45] Date of Patent: Jun. 20, 2000

[54] CYCLOIMIDO-SUBSTITUTED BENZOFUSED HETEROCYCLIC HERBICIDES

[75] Inventors: Scott D. Crawford, Bordentown; Lester L. Maravetz, Westfield; George Theodoridis, Princeton, all of N.J.; Benjamin Dugan, Glen Mills, Pa.

[73] Assignee: FMC Corporation, Philadelphia, Pa.

[21] Appl. No.: 09/028,636

[22] Filed: Feb. 24, 1998

Related U.S. Application Data

[60] Provisional application No. 60/039,172, Feb. 26, 1997.

[51] Int. Cl.⁷ .................. C07D 403/02; A01N 43/54
[52] U.S. Cl. .................. 504/243; 544/309; 544/310; 544/314
[58] Field of Search .................. 544/310; 504/243

[56] References Cited

U.S. PATENT DOCUMENTS

| | | | |
|---|---|---|---|
| 3,920,442 | 11/1975 | Albert et al. | 71/92 |
| 5,354,730 | 10/1994 | Enomoto et al. | 504/243 |
| 5,661,108 | 8/1997 | Crawford et al. | 504/243 |
| 5,753,595 | 5/1998 | Crawford et al. | 504/243 |

FOREIGN PATENT DOCUMENTS

| | | |
|---|---|---|
| 0 255 047 A1 | 3/1988 | European Pat. Off. |
| 0 304 920 A2 | 3/1989 | European Pat. Off. |
| 0 373 461 A2 | 6/1990 | European Pat. Off. |
| 0 476 697 A1 | 3/1992 | European Pat. Off. |
| 0 561 319 A1 | 9/1993 | European Pat. Off. |
| 0 617 033 A1 | 9/1994 | European Pat. Off. |
| 195 04 188 A1 | 8/1996 | Germany. |
| 195 23 640 A1 | 1/1997 | Germany. |
| WO 95/05079 | 2/1995 | WIPO. |
| WO 97/08170 | 3/1997 | WIPO. |
| WO 97/29105 | 8/1997 | WIPO. |
| WO 97/42188 | 11/1997 | WIPO. |

*Primary Examiner*—Richard L. Raymond
*Assistant Examiner*—Deepak R. Rao
*Attorney, Agent, or Firm*—FMC Corporation

[57] ABSTRACT

Novel herbicidal compounds, compositions containing them, and methods for their use in controlling weeds are disclosed. The novel herbicidal compounds are represented by formula I:

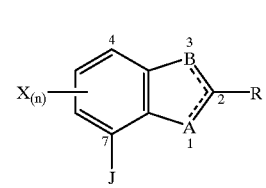

where J is a 1-substituted-6-trifluoromethyl-2,4-pyrimidinedione-3-yl, a 1-substituted-6-trifluoromethyl-1,3,5-triazine-2,4-dion-1-yl, a 3,4,5,6-tetrahydrophthalimid-1-yl, a 4-difluoromethyl-4,5-dihydro-3-methyl-1,2,4-triazol-5(1H)-on-1-yl, a 5,6,7,8-tetrahydro-1H,3H-[1,3,4]thiadiazolo[3,5-a]pyridazineimin-1-yl, or a 1,6,8-triazabicyclo[4.3.0]-nonane-7,9-dion-8-yl ring attached at the 7 position of a benzofuran, benzoxazole, indole, 2,3-dihydrobenzimidazole or benzimidazole, and X is selected from hydrogen, halogen, cyano, nitro, and amino. Preferred R groups are optionally substituted alkyl groups.

20 Claims, No Drawings

CYCLOIMIDO-SUBSTITUTED BENZOFUSED HETEROCYCLIC HERBICIDES

This application claims the benefit of U.S. Provisional Application No. 60/039,172 filed Feb. 26, 1997.

BACKGROUND OF THE INVENTION

The present invention relates generally to novel herbicidal compounds and methods for their use in controlling unwanted plant species in agriculture. In particular, the present invention pertains to cycloimido-substituted benzofused heterocyclic herbicides, and more particularly it pertains to herbicides in which the benzofused heterocycle is a benzofuran, benzimidazole, a 2,3-dihydrobenzimidazole, or indole having a cycloimido moiety which is a 1-substituted-6-trifluoromethyl-2,4-pyrimidinedione-3-yl, a 1-substituted-6-trifluoromethyl-1,3,5-triazine-2,4-dion-1-yl, a 3,4,5,6-tetrahydrophthalimid-1-yl, a 4-difluoromethyl-4,5-dihydro-3-methyl-1,2,4-triazol-5(1H)-on-1-yl, a 5,6,7,8-tetrahydro-1H,3H-[1,3,4]thiadiazolo[3,5-a]pyridazineimin-1-yl, or a 1,6,8-triazabicyclo[4.3.0]-nonane-7,9-dion-8-yl ring.

SUMMARY OF THE INVENTION

It has now been found that certain cycloimido-substituted benzofused heterocyclic compounds are useful as pre-emergent and postemergent herbicides. These novel compounds are represented by formula I:

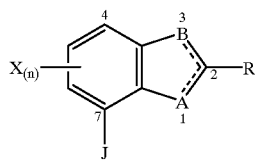

I where J is a 1-substituted-6-trifluoromethyl-2,4-pyrimidinedione-3-yl, a 1-substituted-6-trifluoromethyl-1,3,5-triazine-2,4-dion-1-yl, a 3,4,5,6-tetrahydrophthalimid-1-yl, a 4-difluoromethyl-4,5-dihydro-3-methyl-1,2,4-triazol-5(1H)-on-1-yl, a 5,6,7,8-tetrahydro-1H,3H-[1,3,4]thiadiazolo[3,5-a]pyridazineimin-1-yl, or a 1,6,8-triazabicyclo[4.3.0]-nonane-7,9-dion-8-yl ring attached at the 7 position of a benzofuran, benzoxazole, 2,3-dihydrobenzimidazole, indole or benzimidazole, and X is selected from hydrogen, halogen, cyano, nitro, alkyl, haloalkyl, and amino. Preferred R groups are optionally substituted alkyl groups.

DETAILED DESCRIPTION OF THE INVENTION

Certain cycloimido-substituted benzofused heterocyclic compounds have now been found to be useful as pre- and postemergent herbicides. These compounds are represented by formula I:

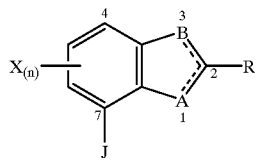

I where
(1) A is nitrogen double-bonded to position 2 and B is oxygen;

(2) A is oxygen and B is $CR^1$ double bonded to position 2;

(3) A is NH and B is nitrogen double-bonded to position 2;

(4) A is nitrogen double bonded to position 2 and B is $NR^2$;

(5) A is CH double bonded to position 2 and B is $NR^2$;

(6) A is NH and B is $CR^1$ double bonded to position 2; or (7) A and B are NH

R is hydrogen, hydroxy, mercapto, straight or branched chain lower alkyl, cycloalkyl, alkoxy, aryl, heteroaryl, alkenyl, haloalkyl, hydroxyalkyl, haloaryl, alkoxyaryl, arylalkyl, aryloxyalkyl, haloarylalkyl, alkylthio, heterocyclyl, alkoxyalkyl, alkoxylalkyloxyalkyl, alkylcarbonyloxyalkyl, arylcarbonyloxyalkyl, aminocarbonyloxyalkyl, aminoalkyl, cyanoalkyl, aminoalkenyl, carboxy, carboxyalkyl, alkylcarboxy, alkylcarboxyalkyl, formyl, aminocarbonyl, amino, oxygen, cyano, nitro, alkylsulfonyl, aminosulfonyl, alkylsulfonylamino, alkoxycarbonyloxyalkyl, alkylcarboxylalkoxy, alkoxycarbonylamino, alkoxycarbonylalkylaminoalkyl, aryliminoalkyl, (aryl)(alkoxy)alkyl, (aryl)(alkylcarbonyloxy)alkyl, arylalkoxyalkyl, cyanoalkylthio, alkynylalkylthio, arylalkylthio, cyanothio, cyanothioalkyl, alkoxycarbonylalkylthio, aminocarbonylalkylthio, alkenylalkylthio, haloalkylalkynylalkylthio, aminocarbonyloxyalkyl, arylalkylcarbonylaminoalkyl, (hydroxy)(aryl)alkyl, alkylcarbonylaminoalkyl, alkylsulfonylaminoalkyl, aminocarbonylalkyl, alkoxycarbonyl, and alkenyloxy, where the amino group may be substituted with one or two substituents independently selected from alkyl, hydroxy, alkoxy, carboxy, aryl, alkylsufonyl, or haloalkylsulfonyl;

$R^1$ is hydrogen, lower alkyl, or haloalkyl;

$R^2$ is hydrogen, alkyl, haloalkyl, $CO_2(alkyl)$, $CH_2CO_2(alkyl)$, $CH_2CONH$—alkyl, $CH_2CON(alkyl)_2$, $CH_2CO_2H$, $CH_2OCH_3$, $SO_2(alkyl)$, $CH_2CH=CH_2$, $CH_2C\equiv CH$.

X is selected from hydrogen, F, Cl, Br, alkyl, haloalkyl, CN, $NO_2$, and $NH_2$;

n is 0–3;

J is selected from

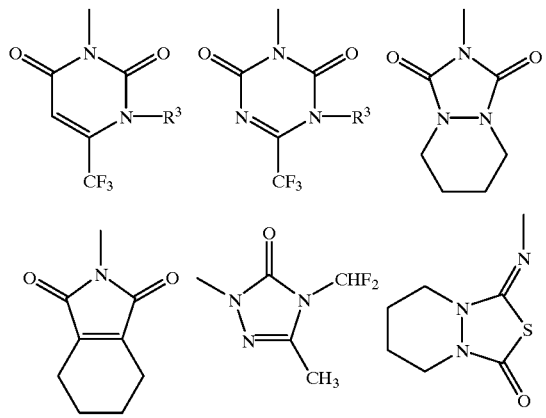

and $R^3$ is selected from hydrogen, alkyl, haloalkyl, $CH_2CN$, $CH_2CH=CH_2$, $CH_2C\equiv CH$, $CH_2CO_2(alkyl)$, $CH_2OCH_3$, and $NH_2$.

Preferred compounds are those of formula I where R is $CH_3$, $CH_2CH_3$, $C(CH_3)_2OH$, $CH_2CH_2OH$, $CH(CH_3)_2$, t-butyl, $CF_3$, $CH(F)CH_3$, $CF_2CF_3$, $C(CH_3)_2OCOCH_3$, $C(CH_3)_2NHSO_2CH_3$, $CH_2CH_2CH_2C\equiv N$, $CH_2CH_2CO_2CH_3$, and $CON(CH_3)_2$; X is a chlorine, bromine or fluorine substituted in one or both of positions 4 and 6; J is

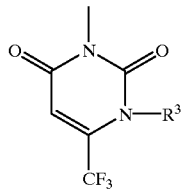

and $R^3$ is $CH_3$ or $NH_2$.

One aspect of the present invention relates to compounds of formula I in which A is nitrogen double-bonded to position 2 and B is oxygen, and R, $R^3$, J, X and n are as described above.

Another aspect of the present invention relates to compounds of formula I in which A is oxygen and B is $CR^1$ double bonded to position 2, and R, $R^1$, $R^3$, J, X and n are as described above.

Another aspect of the present invention relates to compounds of formula I in which A is NH and B is nitrogen double-bonded to position 2, and R, J, X and n are as described above.

Another aspect of the present invention relates to compounds of formula I in which A is nitrogen double bonded to position 2 and B is $NR^2$, and R, $R^2$, $R^3$, J, X and n are as described above.

Another aspect of the present invention relates to compounds of formula I in which A is CH double bonded to position 2 and B is $NR^2$, and R, $R^2$, $R^3$, J, X and n are as described above.

Another aspect of the present invention relates to compounds of formula I in which A is NH and B is $CR^1$ double bonded to position 2, and R, $R^1$, $R^3$, J, X and n are as described above.

Another aspect of the present invention relates to compounds of formula I in which A and B are NH and R, $R^1$, $R^3$, J, X and n are as described above.

Another aspect of the present invention relates to compounds of formula I where J is not

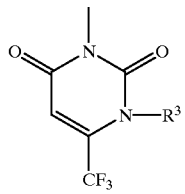

when: A is oxygen and B is $CR^1$ double bonded to position 2; A is CH double bonded to position 2 and B is $NR^2$; or A is NH and B is $CR^1$ double bonded to position 2; and R, $R^1$, $R^3$, X, and n are as described above.

As shown in the specification a wide range of substituents is described for position B in compounds of formula I whereas position A is generally unsubstituted. It was found that some herbicidal activity is retained when a methyl substituent is placed at position A, but that substitution at that position generally causes a sharp decrease in activity.

Certain intermediates of the present invention are novel. These include compounds of formula II:

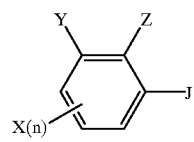

II where Y is $NO_2$, $NH_2$, or $-NHN=C(CH_3)R$; Z is hydrogen, F, $NH_2$, or OH; and R, J, X, and n are as described above; with the proviso that when Y is $-NHN=C(CH_3)R$, Z is hydrogen.

As used in this specification and unless otherwise indicated, the terms "alkyl," "alkenyl," "alkynyl," "haloalkyl," and "alkoxy" used alone or as part of a larger moiety, includes straight or branched carbon chains of 1 to 6 carbon atoms. "Halogen" refers to fluorine, bromine or chlorine. "THF" means tetrahydrofuran, "DMF" means N,N-dimethylformamide, and "DBU" means 1,8-diazabicyclo[5.4.0]undec-7-ene. When "n" in is 2 or 3, the substituents X may be the same or different from one another.

SCHEME 1

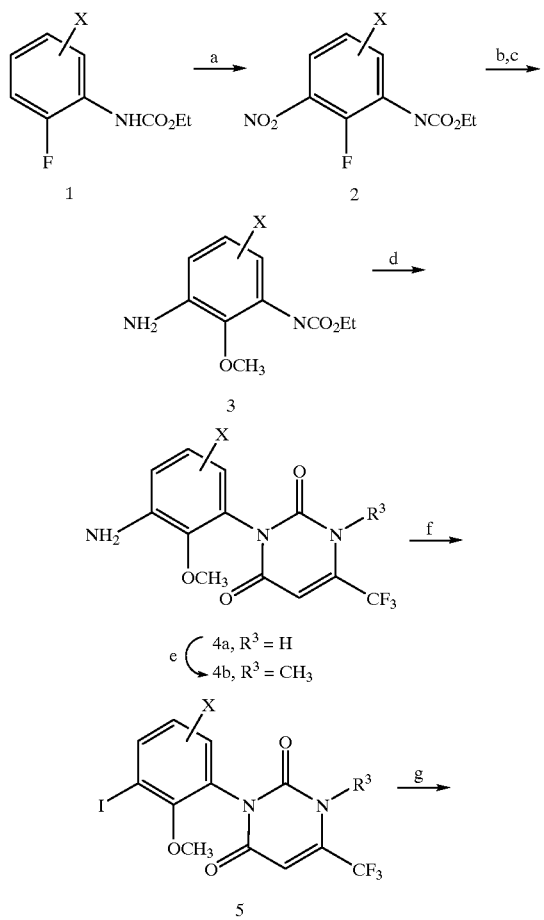

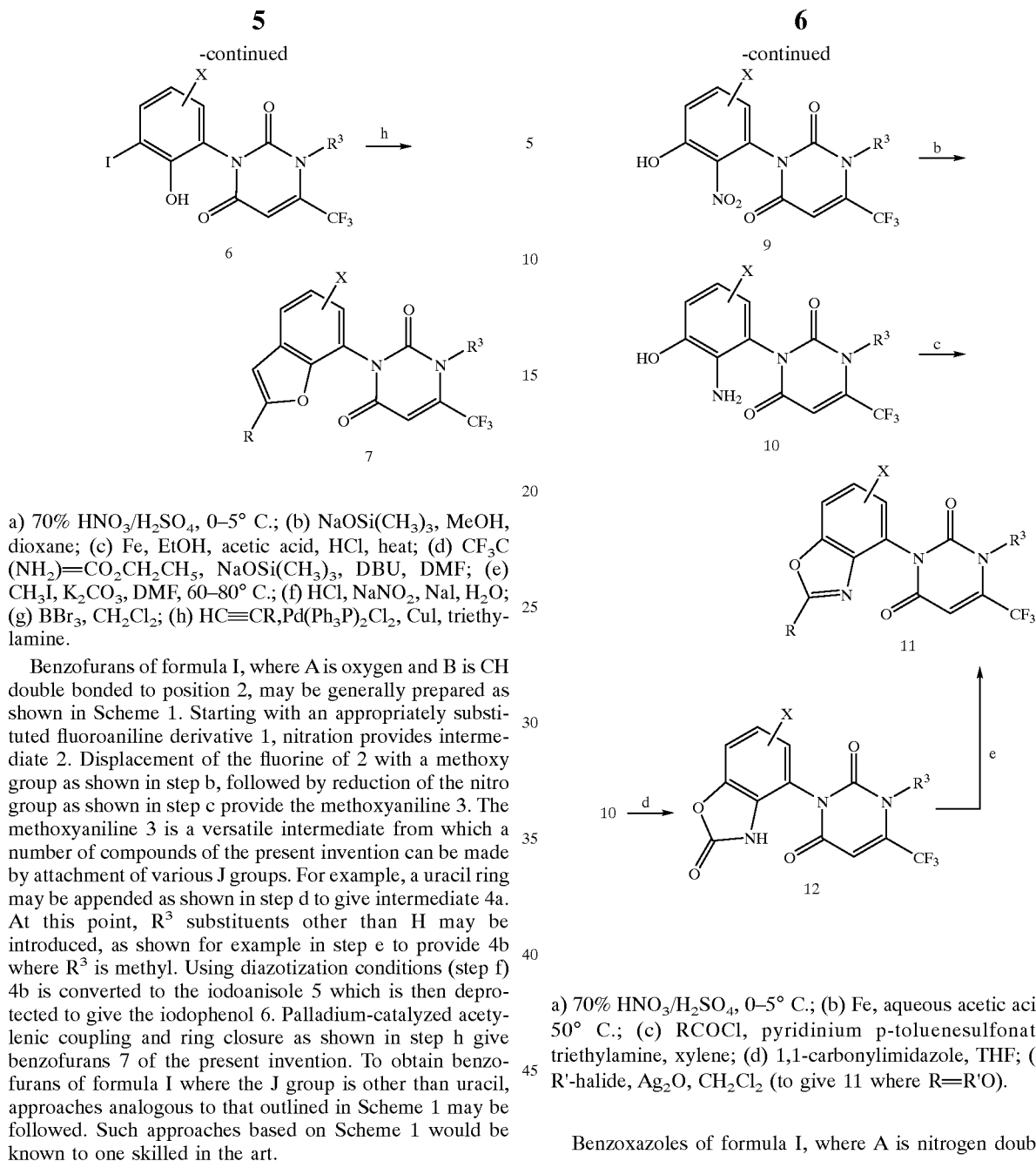

a) 70% HNO$_3$/H$_2$SO$_4$, 0–5° C.; (b) NaOSi(CH$_3$)$_3$, MeOH, dioxane; (c) Fe, EtOH, acetic acid, HCl, heat; (d) CF$_3$C(NH$_2$)=CO$_2$CH$_2$CH$_5$, NaOSi(CH$_3$)$_3$, DBU, DMF; (e) CH$_3$I, K$_2$CO$_3$, DMF, 60–80° C.; (f) HCl, NaNO$_2$, NaI, H$_2$O; (g) BBr$_3$, CH$_2$Cl$_2$; (h) HC≡CR,Pd(Ph$_3$P)$_2$Cl$_2$, CuI, triethylamine.

Benzofurans of formula I, where A is oxygen and B is CH double bonded to position 2, may be generally prepared as shown in Scheme 1. Starting with an appropriately substituted fluoroaniline derivative 1, nitration provides intermediate 2. Displacement of the fluorine of 2 with a methoxy group as shown in step b, followed by reduction of the nitro group as shown in step c provide the methoxyaniline 3. The methoxyaniline 3 is a versatile intermediate from which a number of compounds of the present invention can be made by attachment of various J groups. For example, a uracil ring may be appended as shown in step d to give intermediate 4a. At this point, R$^3$ substituents other than H may be introduced, as shown for example in step e to provide 4b where R$^3$ is methyl. Using diazotization conditions (step f) 4b is converted to the iodoanisole 5 which is then deprotected to give the iodophenol 6. Palladium-catalyzed acetylenic coupling and ring closure as shown in step h give benzofurans 7 of the present invention. To obtain benzofurans of formula I where the J group is other than uracil, approaches analogous to that outlined in Scheme 1 may be followed. Such approaches based on Scheme 1 would be known to one skilled in the art.

Scheme 2

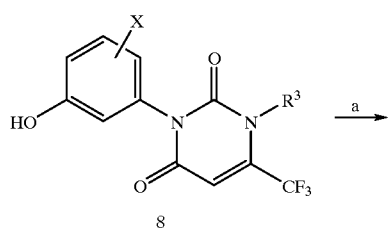

a) 70% HNO$_3$/H$_2$SO$_4$, 0–5° C.; (b) Fe, aqueous acetic acid, 50° C.; (c) RCOCl, pyridinium p-toluenesulfonate, triethylamine, xylene; (d) 1,1-carbonylimidazole, THF; (e) R'-halide, Ag$_2$O, CH$_2$Cl$_2$ (to give 11 where R=R'O).

Benzoxazoles of formula I, where A is nitrogen double bonded to position 2 and B is oxygen, may be prepared as shown in Scheme 2 above. Starting with a phenol such as intermediate 8 nitration under standard conditions gives the nitrophenol 9. Certain of the benzoxazoles 11 of the present invention may be obtained by reduction of 9 to the aniline 10 followed by treatment with an acid halide (such as shown in step c). Alternatively, other benzoxazoles 11 may be obtained by treating 10 with carbonyldiimidazole to give intermediate 12 which can be O-alkyated according to step e. The approach outlined in Scheme 2 can be adapted, in ways known to one skilled in the art, to obtain benzoxazoles of formula I where the J group is other than uracil.

Scheme 3

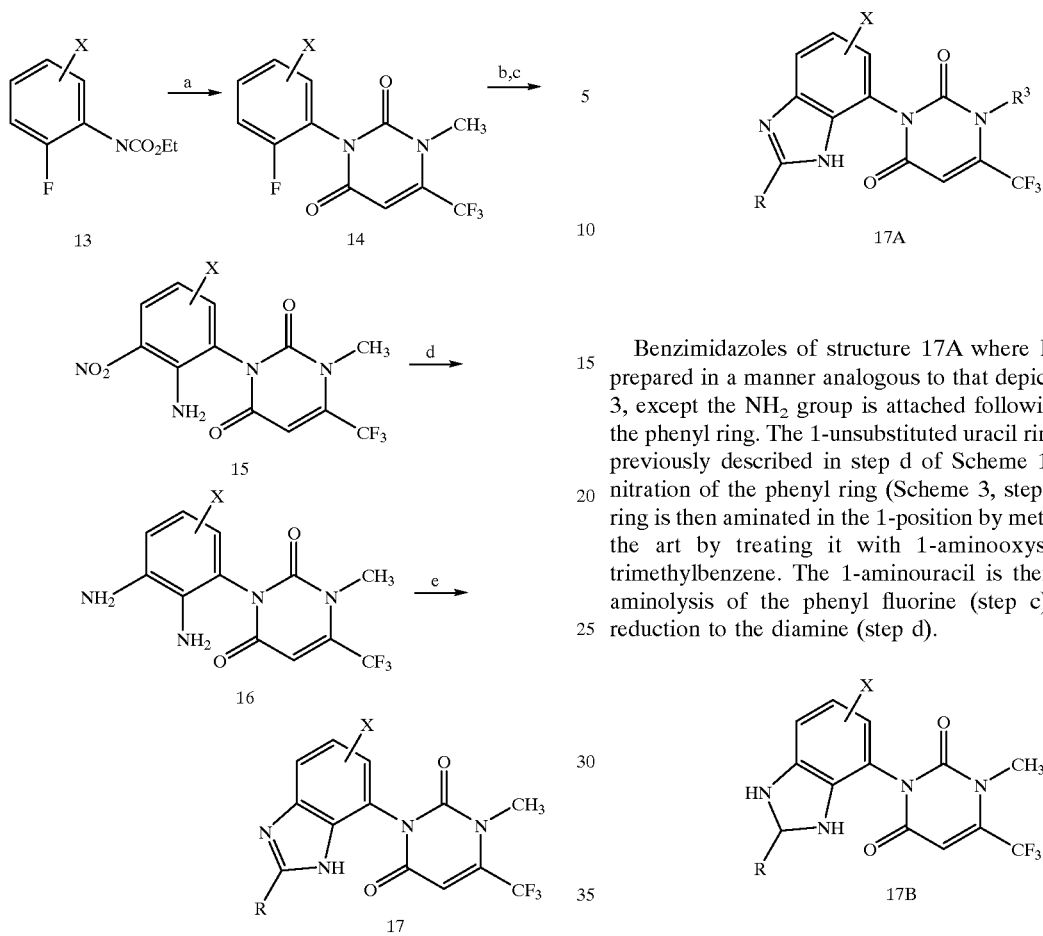

a) see steps (d) and (e) of Scheme 1; (b) 70% $HNO_3/H_2SO_4$, 0–5° C.; (c) $NH_4OAc$, triethylamine, dioxane, heat; (d) $SnCl_2$ $H_2O$ or Fe, $NH_4Cl$, aqueous ethanol, heat; (e) $RCO_2H$, heat; RCO-halide, $CH_2Cl_2$/Pyridine, then $POCl_3$, $CH_2Cl_2$; alkoxycarbonyl isothiocyanate, $HgCl_2$, heat (where R is —$NHCO_2$alkyl); or thiophosgene, EtOAC, heat (where R is —SH).

Benzimidazoles of formula I, where A is NH and B is nitrogen double bonded to position 2, may be prepared as shown in Scheme 3 above. For example, intermediate 13 may be converted to the uracil 14 by the well-known chemistry previously described. Nitration of 14 followed by aminolysis of the fluorine group (steps b and c) provides the nitroaniline 15. The diamine 16 is obtained by reduction of 15 under standard conditions. Benzimidazoles 17 of the present invention are obtained by treatment of 16 with a carboxylic acid, an acid halide, an alkoxycarbonyl isothiocyanate, or thiophosgene according to step e. Other benzimidazoles 17 of the present invention are obtained by derivativization of benzimidazoles depicted in Scheme 3 using techniques known to one skilled in the art. The approach outlined in Scheme 3 can be adapted, in ways known also to one skilled in the art, to obtain benzimidazoles of formula I where the J group is other than uracil.

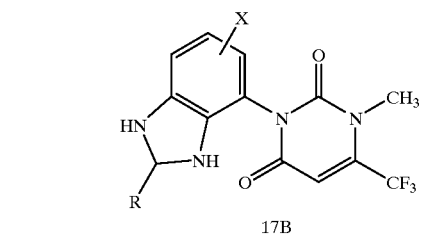

Benzimidazoles of structure 17A where $R^3$ is $NH_2$ are prepared in a manner analogous to that depicted in Scheme 3, except the $NH_2$ group is attached following nitration of the phenyl ring. The 1-unsubstituted uracil ring is formed as previously described in step d of Scheme 1, followed by nitration of the phenyl ring (Scheme 3, step b). The uracil ring is then aminated in the 1-position by methods known in the art by treating it with 1-aminooxysulfonyl-2,4,6-trimethylbenzene. The 1-aminouracil is then subjected to aminolysis of the phenyl fluorine (step c) followed by reduction to the diamine (step d).

2,3-Benzimidazoles of formula I, where A and B are NH may be prepared from Intermediate 16 in Scheme 3 by heating it with an appropriately substituted acetaldehyde ethyl hemiacetal, affording compounds of Structure 17B.

Scheme 4

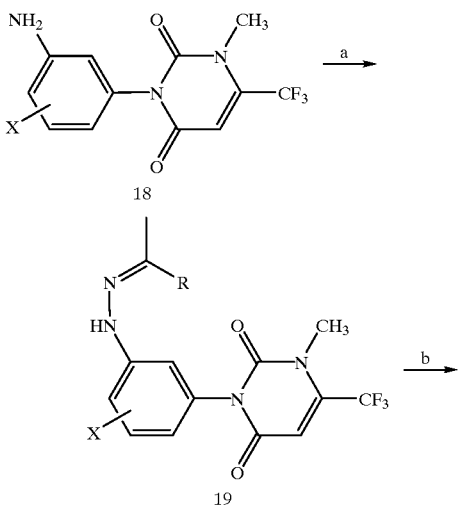

-continued

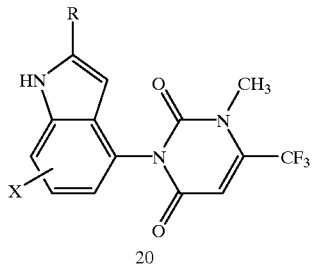
20 a) i. NaNO$_2$, HCl; ii. SnCl$_2$2H$_2$O; iii. RCOCH$_3$; (b) polyphosphoric acid, 80° C.

Indoles of formula I, where A is CH double bonded to position 2 and B is NR$^1$, may be prepared according to Scheme 4 above. Using a Fischer indole route the starting aniline 18 may be converted to the corresponding hydrazone 19 which in turn may be cyclized under acidic conditions such as is shown in step b. The resulting indoles 20 of the present invention may be further derivatized by alkylation of the indole ring nitrogen to indoles of formula I where R$^1$ is other than hydrogen. The approach outlined in Scheme 4 can be adapted, in ways known to one skilled in the art, to obtain indoles of formula I where the J group is other than uracil.

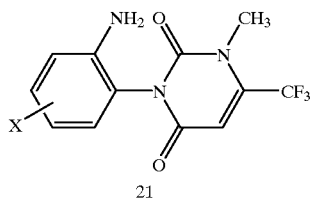
21

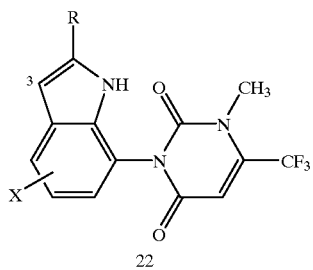
22

Indoles of formula I, where A is NH and B is CR$^1$ double bonded to position 2, may be prepared by a Fischer indole synthesis analogous to that shown in Scheme 4 starting with aniline 21. Substitution at the 3 position of indoles such as 22 with R$^1$ groups is known to one skilled in the art.

Compounds of the present invention may also be prepared in accordance with the procedures shown in the Examples below, by procedures analogous to those shown in the Examples, or by other methods that are generally known or available to one skilled in the art.

EXAMPLE 1

1-Methyl-6-Trifluoromethyl-3-[7-Bromo-5-Fluoro-2-(2-Methylcarbonyloxyprop-2-yl)Benzoxazol-4-yl]-2,4(1H,3H)-Pyrimidinedione (Compound 104)

Step A 1-methyl-6-trifluoromethyl-3-(4-bromo-2-fluoro-5-hydroxy-6-nitrophenyl)-2,4(1H,3H)-pyrimidinedione A stirred solution of 17.0 grams (0.044 mole) of 1-methyl-6-trifluoromethyl-3-(4-bromo-2-fluoro-5-hydroxyphenyl)-2,4(1H,3H)-pyrimidinedione and 5.0 grams (0.050 mole) of sulfuric acid in 100 mL of glacial acetic acid was cooled to 15° C., and 3.2 grams (0.050 mole) of 70% nitric acid was added dropwise. The reaction mixture was then allowed to warm to ambient temperature where it stirred for two hours. The reaction mixture was poured into water and extracted with diethyl ether. The extract was concentrated under reduced pressure to a residue. The residue was purified by column chromatography on silica gel, yielding 16.4 grams of title compound; mp 76–78° C.

Step B 1-methyl-6-trifluoromethyl-3-(6-amino-4-bromo-2-fluoro-5-hydroxyphenyl)-2,4(1H,3H)-pyrimidinedione A stirred solution of 16.0 grams (0.037 mole) of 1-methyl-6-trifluoromethyl-3-(4-bromo-2-fluoro-5-hydroxy-6-nitrophenyl)-2,4(1H,3H)-pyrimidinedione and 10 mL of water in 120 mL of glacial acetic acid was heated to 50° C., and 16.0 grams (excess) of iron dust was slowly added. The reaction mixture was then cooled to ambient temperature where it stirred for one hour. The reaction mixture was filtered through diatomaceous earth, and the filtrate was partitioned in a mixture of 150 mL portions each of water and ethyl acetate. The organic layer was separated, dried with magnesium sulfate, and filtered. The filtrate was concentrated under reduced pressure to a residue. The residue was purified by column chromatography on silica gel, yielding 12.0 grams of title compound; mp 98–100° C.

Step C Compound 104

A stirred solution of 0.50 gram (0.0013 mole) of 1-methyl-6-trifluoromethyl-3-(6-amino-4-bromo-2-fluoro-5-hydroxyphenyl)-2,4(1H,3H)-pyrimidinedione, 0.21 gram (0.0013 mole) of 1-chlorocarbonyl-1-methylethyl acetate, 0.14 gram (0.0014 mole) of triethylamine, and 0.16 gram (0.0006 mole) of pyridinium p-toluenesulfonate in 50 mL of xylene was heated at 150 ° C. for about 18 hours. The reaction mixture was then cooled to ambient temperature and taken up in ethyl acetate. The solution was washed with water and an aqueous solution saturated with sodium chloride; then it was dried with magnesium sulfate. The mixture was filtered, and the filtrate was concentrated under reduced pressure to a residue. The residue was purified by column chromatography on silica gel, yielding 0.72 gram of Compound 104. The NMR spectrum was consistent with the proposed structure.

EXAMPLE 2

1-Methyl-6-Trifluoromethyl-3-(7-Bromo-5-Fluoro-2-Methoxy-Benzoxazol-4-yl-2,4(1H,3H)-Pyrimidinedione (Compound 109)

Step A 1-methyl-6-trifluoromethyl-3-(7-bromo-5-fluorobenzoxazol-2-on-4-yl)-2,4(1H,3H)-pyrimidinedione A stirred solution of 2.0 grams (0.005 mole) of 1-methyl-6-trifluoromethyl-3-(6-amino-4-bromo-2-fluoro-5-hydroxyphenyl)-2,4(1H,3H)-pyrimidinedione and 1.2 grams (0.008 mole) of carbonylimidazole in 50 mL of THF was heated at reflux for three hours. The reaction mixture was cooled and concentrated under reduced pressure to a residue. The residue was purified by column chromatography on silica gel, yielding 1.1 grams of title compound. The NMR spectrum was consistent with the proposed structure.

Step B Compound 109

A mixture of 0.50 gram (0.001 mole) of 1-methyl-6-trifluoromethyl-3-(7-bromo-5-fluorobenzoxazol-2-on-4-yl)-2,4(1H,3H)-pyrimidinedione 0.17 gram (0.001 mole) of methyl iodode, and 0.27 gram (0.001 mole) of silver(1) oxide in 50 mL of methylene chloride was stirred at ambient temperature for two hours. The product was isolated from the reaction mixture by column chromatography on silica gel, yielding 0.28 gram of Compound 109. The NMR spectrum was consistent with the proposed structure.

EXAMPLE 3

1-Methyl-6-Trifluoromethyl-3-[7-Chloro-5-Fluoro-2-(1-Methylethyl)Benzoxazol-4-yl]-2,4(1H,3H)-Pyrimidinedione (Compound 28)

Step A 1-methyl-6-trifluoromethyl-3-(4-chloro-2-fluoro-5-hydroxyphenyl)-2,4(1H,3H)-pyrimidinedione A stirred solution of 18.2 grams (0.054 mole) of 1-methyl-6-trifluoromethyl-3-(5-amino-4-chloro-2-fluorophenyl)-2,4(1H,3H)-pyrimidinedione in 100 mL of sulfuric acid was cooled to 5° C., and a solution of 3.7 grams (0.054 mole) of sodium nitrite in about 10 mL of water was added dropwise. The reaction mixture was then warmed to ambient temperature where it stirred for two hours. In a separate reaction vessel, a stirred mixture of 242 grams (0.970 mole) of copper(II) sulfate and 1.5 grams (0.005 mole) of iron(II) sulfate heptahydrate in about 300 mL of water and 300 mL of xylene was heated to reflux, and the pyrimidinedione diazonium solution prepared above was added dropwise. The reaction mixture was stirred at reflux for two additional hours, then allowed to cool as it stirred for about 18 hours. The reaction mixture was poured into about 600 mL of water, and the aqueous/organic layers were separated. The aqueous layer was washed with ethyl acetate, and the wash was combined with the organic layer. The combined organic material was washed with water, then with an aqueous solution saturated with sodium chloride. The organic material was dried with magnesium sulfate and filtered. The filtrate was concentrated under reduced pressure, yielding impure product. The product was dissolved in diethyl ether and washed with aqueous 10% hydrochloric acid, and with water. The diethyl ether solution was dried with magnesium sulfate and filtered. The filtrate was concentrated under reduced pressure, yielding 7.6 grams of title compound. The NMR spectrum was consistent with the proposed structure.

Step B 1-methyl-6-trifluoromethyl-3-(4-chloro-2-fluoro-5-hydroxy-6-nitrophenyl)-2,4(1H,3H)-pyrimidinedione This compound was prepared in the manner of Step A of Example 1, using 3.8 grams (0.011 mole) of 1-methyl-6-trifluoromethyl-3-(4-chloro-2-fluoro-5-hydroxyphenyl)-2,4(1H,3H)-pyrimidinedione, 1.0 gram (0.011 mole) of 70% nitric acid, and 50 mL of sulfuric acid, yielding 1.5 grams of title compound. The NMR spectrum was consistent with the proposed structure.

Step C 1-methyl-6-trifluoromethyl-3-(6-amino-4-chloro-2-fluoro-5-hydroxy-phenyl)-2,4(1H,3H)-pyrimidinedione This compound was prepared in the manner of Step B of Example 1, using 1.5 grams (0.004 mole) 1-methyl-6-trifluoromethyl-3-(4-chloro-2-fluoro-5-hydroxy-6-nitrophenyl)-2,4(1H,3H)-pyrimidinedione, 3.0 grams (0.054 mole) of iron dust, and 5 mL of water in 50 mL of glacial acetic acid, yielding 1.0 gram of title compound. The NMR spectrum was consistent with the proposed structure.

Step D Compound 28

This compound was prepared in the manner of Step C of Example 1, using 0.52 gram (0.0015 mole) of 1-methyl-6-trifluoromethyl-3-(6-amino4-chloro-2-fluoro-5-hydroxyphenyl)-2,4(1H,3H)-pyrimidinedione, 0.18 gram (0.0017 mole) of isobutyryl chloride, 0.24 gram (0.0017 mole) of triethylamine, and 0.09 gram (0.0004 mole) of pyridinium p-toluenesulfonate in 50 mL of xylene, yielding 0.22 gram of Compound 28. The NMR spectrum was consistent with the proposed structure.

EXAMPLE 4

Synthesis of 3-(4-Chloro-6-Fluoro-2-Phenylbenzofuran-7-yl)-1-Methyl-6-Trifluoromethyl-2,4(1H,3H)-Pyrimidinedione (Compound 280)

Step A ethyl N-(4-chloro-2,6-difluoro-3-nitrophenyl) carbamate

A stirred solution of 23.6 grams (0.109 mole) of ethyl N-(4-chloro-2,6-difluorophenyl)carbamate in 125 mL of concentrated sulfuric acid was cooled to about 0° C. and 7.7 mL (0.123 mole) of 70% nitric acid was added dropwise at a rate to maintain the reaction temperature below 10° C. Upon completion of addition, the reaction mixture was stirred at 10° C. for 30 minutes and then allowed to warm to ambient temperature where it stirred for about 18 hours. At the conclusion of this period, the reaction mixture was poured into 150 mL of ice-water. The resulting precipitate was collected by vacuum filtration and washed with water followed by petroleum ether. The precipitate was dried in a heated vacuum desicator, yielding 30.6 grams of title compound. The NMR spectrum was consistent with the proposed structure.

Step B ethyl N-(4-chloro-6-fluoro-2-methoxy-3-nitrophenyl)carbamate

Under a nitrogen atmosphere, a solution of 30.6 grams (0.109 mole) of ethyl N-(4-chloro-2,6-difluoro-3-nitrophenyl)carbamate and 18 mL (0.449 mole) of methanol in 175 mL of dioxane was stirred and 218 mL (0.218 mole) of 1 M sodium trimethylsilanoate (in tetrahydrofuran) was added dropwise during a 45 minute period. Upon completion of addition, the reaction mixture was heated to 65° C. where it stirred for three hours. At the conclusion of this period, the reaction mixture was allowed to cool to ambient temperature where it stirred for about 18 hours. The reaction mixture was concentrated under reduced pressure to a residue. The residue was taken up in cold 3 N hydrochloric acid. The resulting solid was collected by filtration, washed with petroleum ether, and heat dried under vacuum, yielding 21.3 grams of title compound. The NMR spectrum was consistent with the proposed structure.

Step C ethyl N-(3-amino-4-chloro-6-fluoro-2-methoxyphenyl)carbamate

Under a nitrogen atmosphere, a stirred solution of 21.3 grams (0.072 mole) of ethyl N-(4-chloro-6-fluoro-2-methoxy-3-nitrophenyl)carbamate, 18.3 grams (0.328 mole) of iron powder, 50 mL of acetic acid, and 250 mL of ethanol was heated to 65° C. where it stirred for two hours. At the conclusion of this time, 3 mL (0.036 mole) of 12 M hydrochloric acid was added. Upon completion of addition, the reaction mixture was stirred for an additional two hours. After this time, the reaction mixture was concentrated under reduced pressure to yield a brown oil. The oil was then taken up in methylene chloride. The mixture was filtered through diatomaceous earth, and the filter cake was washed with water and an aqueous saturated sodium bicarbonate solution. The filtrate was stored over sodium sulfate for about 18 hours and then filtered. The solvent was removed under reduced pressure to yield a black oil. This oil was filtered through a silica gel pad, yielding 15.0 grams of ethyl N-(3-amino-4-chloro-6-fluoro-2-methoxyphenyl) carbamate. The NMR spectrum was consistent with the proposed structure.

Step D 3-(3-amino-4-chloro-6-fluoro-2-methoxyphenyl)-6-trifluoromethyl-2,4-(1H,3H)-pyrimidinedione This compound was prepared using 4.0 grams (0.036 mole) of sodium trimethylsilanolate, 6.6 grams (0.036 mole) of ethyl 3-amino-4,4,4-trifluorocrotonate, 8.5 grams (0.032 mole) of ethyl N-(3-amino-4-chloro-6-fluoro-2-methoxyphenyl)carbamate, and 2.2 grams (0.014 mole) of DBU in 75 mL of DMF. This preparation differs from well-known literature preparations for pyrimidinedione rings in that sodium trimethylsilanolate and DBU were used rather than sodium hydride. The yield of title compound was 1.7 grams. The NMR spectrum was consistent with the proposed structure.

Step E 3-(3-amino-4-chloro-6-fluoro-2-methoxyphenyl)-1-methyl-6-trifluoromethyl-2,4(1H,3H)-pyrimidinedione A solution of 7.5 grams (0.021 mole) of 3-(3-amino-4-chloro-6-fluoro-2-methoxyphenyl)-6-trifluoromethyl-2,4-(1H,3H)-pyrimidinedione, 3.4 grams (0.025 mole) of potassium carbonate, and 3.5 grams (0.025 mole) of methyl iodide in 200 mL of acetone was stirred at ambient temperature for about 18 hours. The reaction mixture was then concentrated under reduced pressure, and the residue was taken up in 200 mL of water. The mixture was extracted with two 100 mL portions of ethyl acetate. The combined extracts were washed with two 50 mL portions of an aqueous saturated sodium chloride solution. The organic layer was dried with magnesium sulfate, filtered, and concentrated under reduced pressure, yielding 6.9 grams of crude product. The dark oil was combined with 7.0 grams of crude product prepared by a similar route to yield a total of 13.9 grams of crude product. The crude product was purified by column chromatography on silica gel, yielding 10.0 grams of title compound. The NMR spectrum was consistent with the proposed structure.

Step F 3-(4-chloro-6-fluoro-3-iodo-2-methoxyphenyl)-1-methyl-6-trifluoromethyl-2,4(1H,3H)-pyrimidinedione A solution of 4.0 grams (0.011 mole) of 3-(3-amino-4-chloro-6-fluoro-2-methoxyphenyl)-1-methyl-6-trifluoromethyl-2,4-(1H,3H)-pyrimidinedione in 25 mL (0.300 mole) of concentrated hydrochloric acid was stirred and cooled in an ice bath. During a 15 minute period, 1.9 grams (0.013 mole) of sodium nitrite was added dropwise at a rate to maintain the reaction temperature at 15° C. Upon completion of addition, the mixture was stirred for 20 minutes and then poured into 15.0 grams (0.090 mole) of potassium iodide. The reaction mixture was stirred for 30 minutes and then filtered. The filter cake was thoroughly washed with distilled water and then taken up in 150 mL of ethyl acetate. The resulting solution was dried with sodium sulfate and filtered. The filtrate was concentrated under reduced pressure to yield a brown solid. The solid was subjected to column chromatography on silica gel. Elution was accomplished using 5:1 heptane and ethyl acetate. The product-containing fractions were combined and concentrated under reduced pressure, yielding 3.0 grams of title compound. The NMR spectrum was consistent with the proposed structure.

Step G 3-(4-chloro-6-fluoro-2-hydroxy-3-iodophenyl)-1-methyl-6-trifluoromethyl-2,4(1H,3H)-pyrimidinedione Under a nitrogen atmosphere, a stirred solution of 3.0 grams (0.006 mole) of 3-(4-chloro-6-fluoro-3-iodo-2-methoxyphenyl)-1-methyl-6-trifluoromethyl-2,4(1 H,3H)-pyrimidinedione in 75 mL of methylene chloride was cooled in a dry ice/acetone bath and 22.0 mL (0.022 mole) of 1 M boron tribromide (in methylene chloride) was added dropwise during a 20 minute period. Upon completion of addition, the reaction mixture was allowed to warm to ambient temperature were it stirred for about one hour. At the conclusion of this period, the reaction mixture was poured into 200 mL of water and extracted with two 50 mL portions of methylene chloride. The combined extracts were washed with one 100 mL portion of an aqueous saturated sodium chloride solution, dried with sodium sulfate, and filtered. The filtrate was concentrated under reduced pressure, yielding 2.6 grams of title compound. The NMR spectrum was consistent with the proposed structure.

Step H Compound 280

Under a nitrogen atmosphere, a solution of 1.5 grams (0.003 mole) of 3-(4-chloro-6-fluoro-2-hydroxy-3-iodophenyl)-1-methyl-6-trifluoromethyl-2,4(1H,3H)-pyrimidinedione, 0.41 gram (0.004 mole) of phenylacetylene, and 0.71 gram (0.007 mole) of triethylamine in 25 mL of DMF was stirred. To this was added 0.09 gram (0.00013 mole) of dichlorobis(triphenylphosphine) pallidium (II) and 0.05 gram (0.00026 mole) of copper (I) iodide. Upon completion of addition, the reaction mixture was heated to 70° C. where it stirred for 2.5 hours. After this time, the reaction mixture was cooled to ambient temperature and then poured into 150 mL of an aqueous 10% ammonium chloride solution. The resulting precipitate was collected by filtration and washed with water. The precipitate was taken up in 120 mL of ethyl acetate. The resulting solution was dried with sodium sulfate and filtered. The filtrate was concentrated under reduced pressure to a brown solid. The solid was recrystallized using 1:1 chloroform and petroleum ether, yielding 0.31 gram of Compound 280. The mother liquor was concentrated to a residue. The residue was recrystallized using petroleum ether to yield an additional 0.21 gram of Compound 280, m.p. 215–216° C. The NMR spectrum was consistent with the proposed structure.

EXAMPLE 5

Synthesis of 3-(4-Chloro-6-Fluoro-2-Trifluoromethylbenzimidazol-7-yl)-1-Methyl-6-Trifluoromethyl-2,4(1H,3H)-Pyrimidinedione (Compound 365)

A stirred solution of 3.0 grams (0.0085 mole) of 3-(5,6-diamino-4-chloro-2-fluorophenyl)-1-methyl-6-trifluoromethyl-2,4(1H,3H)-pyrimidinedione in 15.0 mL of trifluoroacetic acid was heated to 65° C. where it stirred for one hour. At the conclusion of this period, the reaction mixture was analyzed by TLC, which indicated that the reaction was not complete. The reaction mixture was stirred at 65° C. for an additional two hours. After this time, the reaction mixture was again analyzed by TLC, which indicated that the reaction was complete. The reaction mixture was allowed to cool to ambient temperature and then poured into 200 mL of water. The resulting mixture was allowed to stand at ambient temperature for about 18 hours. At the conclusion of this period, the resulting solid was collected by filtration and washed with water followed by heptane. The filter cake was dried under vacuum, yielding 3.6 grams of Compound 365, m.p. 130° C. The NMR spectrum was consistent with the proposed structure.

EXAMPLE 6

Synthesis of 3-(4-Chloro-2-Ethyl-6-Fluorobenzimidazol-7-yl)-1-Methyl-6-Trifluoromethyl-2,4(1H,3H)-Pyrimidinedione (Compound 367)

Step A 3-(4-chloro-2,6-difluorophenyl)-1-methyl-6-trifluoromethyl-2,4-(1H,3H)-pyrimidinedione Under a nitrogen atmosphere, a solution of 32.0 grams (0.900 mole) of sodium hydride (60% by weight) in 250 mL of DMF was vigorously stirred and cooled in an ice bath. To this a solution of 133.0 grams (0.726 mole) of ethyl 3-amino-4,4,4-trifluorocrotonate in 150 mL of DMF was added dropwise at a rate to maintain the reaction mixture temperature at about 5° C. Upon completion of addition, a solution of 156.3 grams (0.663 mole) of ethyl N-(4-chloro-2,6-difluorophenyl)carbamate in 250 mL of DMF was added dropwise. Upon completion of addition, the mixture was removed from the ice bath and heated to 130° C. where it stirred for 3.5 hours. After this time, the mixture was analyzed by gas chromatography (GC), which indicated that only a slight amount of the starting material was left. The mixture was cooled to 5° C. and 83.0 mL (1.333 moles) of methyl iodide was added dropwise at a rate to maintain the reaction mixture temperature below 20° C. Upon completion of addition, the reaction mixture was allowed to warm to ambient temperature where it stirred for about 18 hours. At the conclusion of this period, the reaction mixture was filtered through diatomaceous earth. The filtrate was concentrated under reduced pressure to yield a dark viscous oil. The oil was taken up in methylene chloride and washed with three 1000 mL portions of water followed by one 1000 mL portion of an aqueous saturated sodium chloride solution. The organic layer was dried with magnesium sulfate, filtered, and concentrated under reduced pressure, yielding 223.8 grams of title compound. The NMR spectrum was consistent with the proposed structure.

Step B 3-(4-chloro-2,6-difluoro-5-nitrophenyl)-1-methyl-6-trifluoromethyl-2,4(1H,3H)-pyrimidinedione A stirred solution of 211.0 grams (0.619 mole) of 3-(4-chloro-2,6-difluorophenyl)-1-methyl-6-trifluoromethyl-2,4(1H,3H)-pyrimidinedione in 600 mL of concentrated sulfuric acid was cooled to less than 10° C., and 44 mL (0.689 mole) of aqueous 70% nitric acid was added dropwise at a rate to maintain the reaction temperature below 10° C. Upon completion of addition, the reaction mixture was analyzed by GC, which indicated the reaction was incomplete. The reaction was allowed to warm to ambient temperature and an additional 5 mL (0.078 mole) of aqueous 70% nitric acid was added. The reaction mixture was again analyzed by GC, which indicated the reaction was complete. The reaction mixture was poured into ice-water. The resulting solid was collected by filtration, washed with water, and then taken up in 600 mL of methylene chloride. The resulting solution was washed with two 600 mL portions of water, one 600 mL portion of an aqueous saturated sodium bicarbonate solution, and one 600 mL portion of an aqueous saturated sodium chloride solution. The organic layer was separated, dried with magnesium sulfate, and filtered. The filtrate was concentrated under reduced pressure, yielding a waxy tan solid. The solid was triturated with heptane and allowed to stand for about 72 hours. At the conclusion of this period, the solid was collected by filtration, washed with heptane, and dried under reduced pressure, yielding 201.4 grams of title compound. The NMR spectrum was consistent with the proposed structure.

Step C 3-(6-amino4-chloro-2-fluoro-5-nitrophenyl)-1-methyl-6-trifluoromethyl-2,4(1H,3H)-pyrimidinedione To stirred solution of 200 grams (0.519 mole) of 3-(4-chloro-2,6-difluoro-5-nitrophenyl)-1-methyl-6-trifluoromethyl-2,4(1H,3H)-pyrimidinedione in 1000 mL of dioxane was added 150 mL (1.091 moles) of triethylamine in one portion. Upon completion of addition, the mixture was vigorously stirred and 400 grams (5.189 moles) of ammonium acetate was added in one portion. The reaction mixture was heated to 90° C. where it stirred for two hours. The reaction mixture was allowed to cool to ambient temperature where it stirred for about 18 hours. The resulting suspension was collected by filtration and washed with dioxane. The filtrate was concentrated under reduced pressure to yield a viscous dark oil. The oil was poured into ice-water. The resulting solid was collected by filtration and washed with water. The solid was dried under reduced pressure and then at ambient temperature for about 18 hours, yielding 195.1 grams of title compound. The NMR spectrum was consistent with the proposed structure.

Step D 3-(5,6-diamino-4-chloro-2-fluorophenyl)-1-methyl-6-trifluoromethyl-2,4-(1H,3H)-pyrimidinedione and 3-(5,6-diamino-4-chloro-2-fluorophenyl)-1-methyl-6-trifluoromethyl-2,4(1H,3H)-pyrimidinedione A solution of 278.0 grams (1.232.moles) of tin(II) chloride dihydrate, 264.0 grams (4.936 moles) of ammonium chloride, 400 mL of water. and 800 mL of ethanol was vigorously stirred, and 157.4 grams (0.411 mole) of 3-(6-amino-4-chloro-2-fluoro-5-nitrophenyl)-1-methyl-6-trifluoromethyl-2,4(1H,3H)-pyrimidinedione was added. Upon completion of addition, the reaction mixture was heated to 83–85° C. where it stirred for 18 hours. After this time the reaction mixture was allowed to cool to ambient temperature. The resultant solid by-product was collected by filtration and washed with ethanol. The combined filtrate and wash was concentrated under reduced pressure to yield a suspension of additional by-product. The suspension was taken up in ethyl acetate and the resultant emulsion was filtered through a pad of diatomaceous earth. The filter cake was washed with ethyl acetate, and the combined organics were washed with three 200 mL portions of water. The organic layer was dried with magnesium sulfate, filtered, and concentrated under reduced pressure to a brown residue. The residue was triturated with heptane and allowed to stand for about five days. The resultant solid was collected by filtration and dried, yielding 144.4 grams of crude product. The crude product was combined with material prepared by a similar route, yielding a total of 157.8 grams of material. The combined product was subjected to column chromatography on silica gel, yielding 83.2 grams of an orange solid. The solid was slurried with warm ethyl acetate, and the insoluble product was collected by filtration. The product was washed with ethyl acetate, and the wash and filtrate from above were combined. The process of concentrating the filtrate, and slurrying the solid residue was repeated twice more, yielding a total of 51.9 grams of title compound. The NMR spectrum was consistent with the proposed structure.

An alternate method for preparing 3-(5,6-diamino-4-chloro-2-fluorophenyl)-1-methyl-6-trifluoromethyl-2,4(1H,3H)-pyrimidinedione is the following:

A solution of 19.2 grams (0.050 mole) of 3-(6-amino-4-chloro-2-fluoro-5-nitrophenyl)-1-methyl-6-trifluoromethyl-2,4(1H,3H)-pyrimidinedione, 3.0 grams (0.056 mole) of ammonium chloride, and 50 mL of water in 100 mL of ethanol was stirred, and 11.2 grams (0.201 mole) of iron powder (325 mesh) was added in one portion. Upon completion of addition, the reaction mixture was heated at reflux for one hour. The reaction mixture was allowed to cool to ambient temperature, then it was filtered through diatomaceous earth to remove the iron powder. The filter cake was washed with 200 mL of acetone, and the wash was combined with the filtrate. The combination was stirred with decolorizing carbon and filtered. The filtrate was concentrated under reduced pressure, yielding a dark brown oil. The oil was then taken up in 200 mL of methylene chloride and washed with three 100 mL portions of an aqueous saturated sodium bicarbonate solution. The organic layer was dried with magnesium sulfate, filtered, and concentrated under reduced pressure, yielding 12.8 grams of title compound. The NMR spectrum was consistent with the proposed structure.

Step E Compound 367

A stirred solution of 1.0 grams (0.0028 mole) of 3-(5,6-diamino-4-chloro-2-fluorophenyl)-1-methyl-6-trifluoromethyl-2,4(1H,3H)-pyrimidinedione and 0.28 mL (0.0035 mole) of pyridine in 10 mL chloroform was cooled to 5° C. and 0.27 mL (0.0031 mole) of propionyl chloride was added dropwise. Upon completion of addition, the mixture was allowed to warm to ambient temperature were it stirred for about 18 hours. The mixture was cooled to 5° C. and 5.0 mL (0.054 mole) of phosphorous oxychloride was added in one portion. Upon completion of addition, the reaction mixture was allowed to warm to ambient temperature where it stirred for about 18 hours. At the conclusion of this period, the reaction mixture was poured into 200 mL of cold water, the resulting mixture was stirred for one hour, then it was extracted with three 50 mL portions of chloroform. The combined extracts were dried with magnesium sulfate and filtered. The filtrate was concentrated under reduced pressure, yielding 0.15 gram of an orange residue. The aqueous layer was made basic with an aqueous saturated sodium bicarbonate solution to a pH of 3–4. The resulting mixture was extracted with three 50 mL portions of methylene chloride. The extracts were combined, dried with magnesium sulfate, and filtered. The filtrate was concentrated under reduced pressure, yielding 0.70 gram of a yellow residue. The yellow residue was triturated with hot heptane. The resulting solid was collected by filtration and washed with heptane, yielding 0.67 gram of Compound 367, m.p. 150–155° C. The NMR spectrum was consistent with the proposed structure.

EXAMPLE 7

Synthesis of 3-(2-t-Butyl-4-Chloro-6-Fluorobenzimidazol-7-yl)-1-Methyl-6-Trifluoromethyl-2,4(1H,3H)-Pyrimidinedione (Compound 369)

To a stirred solution of 1.0 grams (0.0028 mole) of 3-(5,6-diamino-4-chloro-2-fluorophenyl)-1-methyl-6-trifluoromethyl-2,4(1H,3H)-pyrimidinedione, 15.0 mL of ethanol, and 4 mL of 5 M hydrochloric acid was added 1.2 mL (0.0057 mole) of 2,2,6,6-tetramethyl-3,5-heptanedione. Upon completion of addition, the reaction mixture was heated to reflux where it stirred for ten minutes. At the conclusion of this period, the reaction mixture was analyzed by TLC, which indicated that the reaction was not complete. The reaction mixture was stirred at reflux for an additional two hours. After this time, the reaction mixture was again analyzed by TLC, which again indicated that the reaction was still not complete. As a result, an additional 1.0 mL (0.0048 mole) of 2,2,6,6-tetramethyl-3,5-heptanedione was added. Upon completion of addition, the reaction mixture was stirred at reflux for three days. At the conclusion of this period, more ethanol was added to replace that which evaporated, and the reaction mixture was analyzed by TLC for a third time. The reaction mixture was allowed to cool to ambient temperature, poured into 100 mL of an aqueous saturated sodium bicarbonate solution, and 100 mL of chloroform was added. The aqueous layer was separated and washed with two 100 mL portions of chloroform. The chloroform layer and washes were combined, dried with magnesium sulfate, and filtered. The filtrate was treated with decolorizing carbon and stirred. The mixture was filtered and concentrated under reduced pressure to yield a red oil. The oil was taken up in heptane. The resulting solid was collected by filtration and washed with heptane to yield a tan solid. The solid was purified by column chromatography on silica gel, yielding 0.36 gram of Compound 369, m.p. 125–130° C. The NMR spectrum was consistent with the proposed structure.

EXAMPLE 8

Synthesis of 3-(7-Chloro-Fluoro-2-Trifluoromethylindol-4-yl)-1-Methyl-6-Trifluoromethyl-2,4(1H,3H)-Pyrimidinedione (Compound 500)

Step A 3-[5-(1-trifluoromethylethylidenehydrazino)-4-chloro-2-fluorophenyl]-1-methyl-6-trifluoromethyl-2,4(1H,3H)-pyrimidinedione A solution of 3.37 grams (0.010 mole) of 3-(5-amino-4-chloro-2-fluorophenyl)-1-methyl-6-trifluoromethyl-2,4(1H,3H)-pyrimidinedione in 80 mL of concentrated hydrochloric acid was stirred at 25° C. for 20 minutes. After this time, the solution was cooled to 10° C. and a solution of 0.69 gram (0.010 mole) of sodium nitrite in 10 mL of water was slowly added. Upon completion of addition, the mixture was stirred for one hour at 10° C. and then a solution of 5.64 grams (0.025 mole) of tin (II) chloride dihydrate in 40 mL of concentrated hydrochloric acid was slowly added. Upon completion of addition, the reaction mixture was warmed to 25° C. where it stirred for one hour. At the conclusion of this period, 1.12 grams (0.010 mole) of trifluoroacetone was added and the resulting solid was collected by filtration, yielding 3.13 grams of title compound, m.p. 213–214° C. The NMR spectrum was consistent with the proposed structure.

Step B Compound 500

A stirred solution of 2.0 grams (0.0044 mole) of 3-[5-(1-trifluoromethylethylidenehydrazino)-4-chloro-2-fluorophenyl]-1-methyl-6-trifluoromethyl-2,4(1H,3H)-pyrimidinedione in 80 mL of polyphosphoric acid was heated at 80° C. for 20 minutes. After this time, the reaction mixture was allowed to cool to 25° C. where it was diluted with water. The resulting solid was collected by filtration, yielding 0.73 gram of Compound 500, m.p. 208–210° C. The NMR spectrum was consistent with the proposed structure.

EXAMPLE 9

Synthesis of 347-Chloro-2-Ethoxycarbonylindol4-yl)-4,5,6,7-Tetrahydro-1H-Isoindole-1,3(2H)-Dione (Compound 595)

Step A 3-(1-ethoxycarbonylethylidenehydrazino)-4-chloronitrobenzene

This compound was prepared in the manner of Step A, Example 1, using, 17.25 grams (0.10 mole) of 2-chloro-5-nitroaniline, 6.9 grams (0.10 mole) of sodium nitrite, 56.4 grams (0.25 mole) of tin (II) chloride dihydrate, 11.61 grams (0.10 mole) of ethyl pyruvate, 30 mL of water, and 100 mL of concentrated hydrochloric acid. This preparation differs in that ethyl pyruvate was used rather than trifluoroacetone. The yield of title compound was 19.4 grams. The NMR spectrum was consistent with the proposed structure.

Step B 7-chloro-2-ethoxycarbonyl-4-nitroindole

This compound was prepared in the manner of Step B, Example 8, using 14.0 grams (0.050 mole) of 3-(1-ethoxycarbonylethylidenehydrazino)-4-chloronitrobenzene in 100 mL of polyphosphoric acid. The yield of title compound was 0.4 gram. The NMR spectrum was consistent with the proposed structure.

Step C 7-amino-4-chloro-2-ethoxycarbonylindole

A stirred solution of 2.68 grams (0.01 mole) of 4-chloro-2-ethoxycarbonyl-7-nitroindole, 80 mL of acetic acid, and 15 mL of water was heated to 65° C., and 18.3 grams (0.048 mole) of iron powder was slowly added during a 20 minute period. Upon completion of addition, the reaction mixture was allowed to cool to 25° C. where it stirred for one hour. After this time, the reaction mixture was poured into water, and the resulting mixture was filtered through diatomaceous earth. The filter cake was washed thoroughly with ethyl acetate. The organic layer was dried with magnesium sulfate and filtered. The filtrate was concentrated under reduced pressure a residue. The residue was purified by column chromatography, yielding 0.4 gram of title compound. The NMR spectrum was consistent with the proposed structure.

Step D Compound 595

A stirred solution of 0.4 gram (0.0016 mole) of 7-amino-4-chloro-2-ethoxycarbonylindole and 0.26 gram (0.0016 mole) of 3,4,5,6-tetrahydrophhalic anhydride in 80 mL of acetic acid was heated at reflux for about 18 hours. After this time, the reaction mixture was extracted with several portions of diethyl ether. The organic extracts were combined, dried with magnesium sulfate, and filtered. The filtrate was concentrated under reduced pressure to a residue. The residue was purified by column chromatography on silica gel, yielding 0.47 gram of Compound 595. The NMR spectrum was consistent with the proposed structure.

TABLE 1

Benzoxazoles

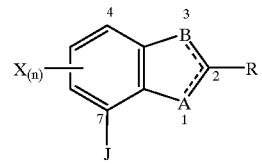

where A is nitrogen double bonded to position 2 and B is O; J is

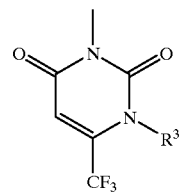

| Compound No. | X | R | R3 |
|---|---|---|---|
| 1 | 4-Cl, 6-F | $CH_3$ | $CH_3$ |
| 2 | 4-Cl, 6-F | $CH_3$ | $C_2H_5$ |
| 3 | 4-Cl, 6-F | $CH_3$ | $CH_2CN$ |
| 4 | 4-Cl, 6-F | $CH_3$ | $CH_2CH=CH_2$ |
| 5 | 4-Cl, 6-F | $CH_3$ | $NH_2$ |
| 6 | 4-Cl, 6-F | $CH_3$ | $CH_2C\equiv CH$ |
| 7 | 4-Cl, 6-F | $CH_3$ | $C_3H_7$ |
| 8 | 4-Cl, 6-F | $CH_3$ | $CH_2OCH_3$ |
| 9 | 4-Cl, 6-F | $CH_3$ | $CH_2CO_2C_2H_5$ |

TABLE 2

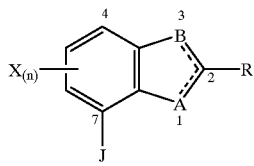

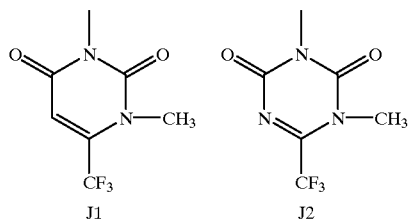

TABLE 2-continued

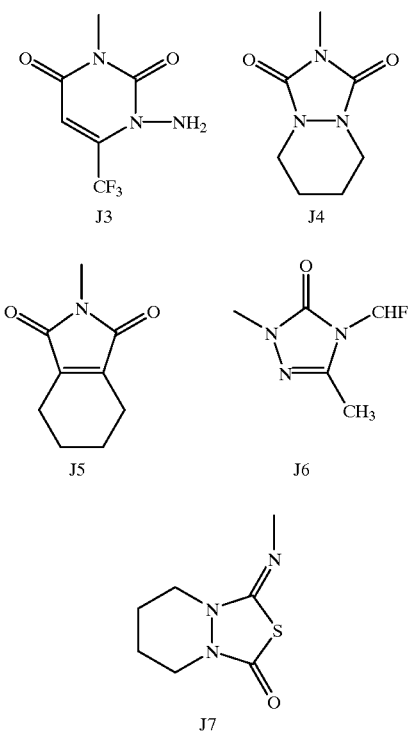

| No. | A | B | Double Bond Posit'n | X | R | J |
|---|---|---|---|---|---|---|
| 10 | N | O | 1-2 | 4-Cl | $CH_3$ | J1 |
| 11 | N | O | 1-2 | 4-Cl | $C_2H_5$ | J1 |
| 12 | N | O | 1-2 | 4-Cl | $CH(CH_3)_2$ | J1 |
| 13 | N | O | 1-2 | 4,6-$Cl_2$ | $CH_3$ | J1 |
| 14 | N | O | 1-2 | 4,6-$Cl_2$ | $C_2H_5$ | J1 |
| 15 | N | O | 1-2 | 4,6-$Cl_2$ | $C_2H_5$ | J1 |
| 16 | N | O | 1-2 | 4-Br, 6-F | $CH_3$ | J1 |
| 17 | N | O | 1-2 | 4-$CF_3$, 6-F | $CH_3$ | J1 |
| 18 | N | O | 1-2 | 4,6-$F_2$ | $CH_3$ | J1 |
| 19 | N | O | 1-2 | 4-CN, 6-F | $CH_3$ | J1 |
| 20 | N | O | 1-2 | 4-$OCF_3$, 6-F | $CH_3$ | J1 |
| 21 | N | O | 1-2 | 4-Br, 6-F | $C_2H_5$ | J1 |
| 22 | N | O | 1-2 | 4-CN, 6-F | $C_2H_5$ | J1 |
| 23 | N | O | 1-2 | 4-CN, 6-F | $CH(CH_3)_2$ | J1 |
| 24 | N | O | 1-2 | 4-$CH_3$, 6-F | $CH_3$ | J1 |
| 25 | N | O | 1-2 | 4-Cl, 6-F | $C_2H_5$ | J1 |
| 26 | N | O | 1-2 | 4-Cl, 6-F | $C_3H_7$ | J1 |
| 27 | N | O | 1-2 | 4-Cl, 6-F | $C_4H_9$ | J1 |
| 28 | N | O | 1-2 | 4-Cl, 6-F | $CH(CH_3)_2$ | J1 |
| 29 | N | O | 1-2 | 4-Cl, 6-F | $CH_2CH(CH_3)_2$ | J1 |
| 30 | N | O | 1-2 | 4-Cl, 6-F | $C(CH_3)_3$ | J1 |
| 31 | N | O | 1-2 | 4-Cl, 6-F | phenyl | J1 |
| 32 | N | O | 1-2 | 4-Cl, 6-F | phenylmethyl | J1 |
| 33 | N | O | 1-2 | 4-Cl, 6-F | $CF_3$ | J1 |
| 34 | N | O | 1-2 | 4-Cl, 6-F | $CCl_2$ | J1 |
| 35 | N | O | 1-2 | 4-Cl, 6-F | Cl | J1 |
| 36 | N | O | 1-2 | 4-Cl, 6-F | OH | J1 |
| 37 | N | O | 1-2 | 4-Cl, 6-F | Br | J1 |
| 38 | N | O | 1-2 | 4-Cl, 6-F | $NH_2$ | J1 |
| 39 | N | O | 1-2 | 4-Cl, 6-F | $NHCH_3$ | J1 |
| 40 | N | O | 1-2 | 4-Cl, 6-F | $N(CH_3)_2$ | J1 |
| 41 | N | O | 1-2 | 4-Cl, 6-F | $NHCH_2CO_2CH_3$ | J1 |
| 42 | N | O | 1-2 | 4-Cl, 6-F | $NHSO_2CH_3$ | J1 |
| 43 | N | O | 1-2 | 4-Br, 6-F | $NHCOCH_3$ | J1 |
| 44 | N | O | 1-2 | 4-Cl, 6-F | morpholino | J1 |
| 45 | N | O | 1-2 | 4-Cl, 6-F | $NHSO_2C_6H_5$ | J1 |
| 46 | N | O | 1-2 | 4-Cl, 6-F | $NHSO_2CH_2C_6H_5$ | J1 |
| 47 | N | O | 1-2 | 4-Cl, 6-F | $N(CH_3)SO_2CH_3$ | J1 |
| 48 | N | O | 1-2 | 4-Cl, 6-F | $NHPO(OCH_3)_2$ | J1 |

TABLE 2-continued

| | | | | | | |
|---|---|---|---|---|---|---|
| 49 | N | O | 1-2 | 4-Br, 6-F | $CH_2CO_2CH_3$ | J1 |
| 50 | N | O | 1-2 | 4-Cl, 6-F | $C_2H_4CO_2CH_3$ | J1 |
| 51 | N | O | 1-2 | 4-Cl, 6-F | $CH=CHCO_2CH_3$ | J1 |
| 52 | N | O | 1-2 | 4-Cl, 6-F | $CH=C(Cl)CO_2CH_3$ | J1 |
| 53 | N | O | 1-2 | 4-Cl, 6-F | $CH_2CH(Cl)CO_2CH_3$ | J1 |
| 54 | N | O | 1-2 | 4-Cl, 6-F | $OCH_3$ | J1 |
| 55 | N | O | 1-2 | 4-Cl, 6-F | $OC_2H_5$ | J1 |
| 56 | N | O | 1-2 | 4-Cl, 6-F | $OCH(CH_3)_2$ | J1 |
| 57 | N | O | 1-2 | 4-Cl, 6-F | $OCH_2CH=CH_2$ | J1 |
| 58 | N | O | 1-2 | 4-Cl, 6-F | $OCH_2C(CH_3)=CH_2$ | J1 |
| 59 | N | O | 1-2 | 4-Cl, 6-F | $OCH_2CCH$ | J1 |
| 60 | N | O | 1-2 | 4-Cl, 6-F | $OCH_2CO_2C_2H_5$ | J1 |
| 61 | N | O | 1-2 | 4-Cl, 6-F | $OCH(CH_3)CO_2CH_3$ | J1 |
| 62 | N | O | 1-2 | 4-Cl, 6-F | $OCH_2CN$ | J1 |
| 63 | N | O | 1-2 | 4-Cl, 6-F | $OCH_2CONH_2$ | J1 |
| 64 | N | O | 1-2 | 4-Cl, 6-F | $OCH_2CONHCH_3$ | J1 |
| 65 | N | O | 1-2 | 4-Cl, 6-F | $OCH(CH_3)CONH_2$ | J1 |
| 66 | N | O | 1-2 | 4-Cl, 6-F | $OCH(CH_3)CONHCH_3$ | J1 |
| 67 | N | O | 1-2 | 4-Cl, 6-F | $OCH_2CO_2H$ | J1 |
| 68 | N | O | 1-2 | 4-Cl, 6-F | phenoxy | J1 |
| 69 | N | O | 1-2 | 4-Cl, 6-F | $p-OC_6H_4OCH(CH_3)CO_2CH_3$ | J1 |
| 70 | N | O | 1-2 | 4-Cl, 6-F | 4-chlorophenoxy | J1 |
| 71 | N | O | 1-2 | 4-Cl, 6-F | phenylmethoxy | J1 |
| 72 | N | O | 1-2 | 4-Cl, 6-F | CN | J1 |
| 73 | N | O | 1-2 | 4-Cl, 6-F | $CO_2CH_3$ | J1 |
| 74 | N | O | 1-2 | 4-Cl, 6-F | $CO_2H$ | J1 |
| 75 | N | O | 1-2 | 4-Cl, 6-F | $CO_2Na$ | J1 |
| 76 | N | O | 1-2 | 4-Cl, 6-F | $CONH_2$ | J1 |
| 77 | N | O | 1-2 | 4-Cl, 6-F | $CONHCH_3$ | J1 |
| 78 | N | O | 1-2 | 4-Cl, 6-F | $CON(CH_3)_2$ | J1 |
| 79 | N | O | 1-2 | 4-Cl, 6-F | $CONHSO_2CH_3$ | J1 |
| 80 | N | O | 1-2 | 4-Cl, 6-F | $CO_2NHOCH_3$ | J1 |
| 81 | N | O | 1-2 | 4-Cl, 6-F | $SCH_3$ | J1 |
| 82 | N | O | 1-2 | 4-Cl, 6-F | $SCH_2CO_2CH_3$ | J1 |
| 83 | N | O | 1-2 | 4-Cl, 6-F | $SCH_2CONH_2$ | J1 |
| 84 | N | O | 1-2 | 4-Cl, 6-F | $SO_2CH_3$ | J1 |
| 85 | N | O | 1-2 | 4-Cl, 6-F | SH | J1 |
| 86 | N | O | 1-2 | 4-Cl, 6-F | $CH_2OH$ | J1 |
| 87 | N | O | 1-2 | 4-Cl, 6-F | $CH(CH_3)OH$ | J1 |
| 88 | N | O | 1-2 | 4-Cl, 6-F | $C(CH_3)_2OH$ | J1 |
| 89 | N | O | 1-2 | 4-Cl, 6-F | $C_2H_4OH$ | J1 |
| 90 | N | O | 1-2 | 4-Cl, 6-F | $CH_2CH(CH_3)OH$ | J1 |
| 91 | N | O | 1-2 | 4-Cl, 6-F | $CH_2C(CH_3)_2OH$ | J1 |
| 92 | N | O | 1-2 | 4-Cl, 6-F | $C(CH_3)_2OCOCH_3$ | J1 |
| 93 | N | O | 1-2 | 4-Cl, 6-F | $CH(CH_3)_2OCOCH_3$ | J1 |
| 94 | N | O | 1-2 | 4-Cl, 6-F | $CH(CH_3)OCOCH_3$ | J1 |
| 95 | N | O | 1-2 | 4-Cl, 6-F | $CHBr_2$ | J1 |
| 96 | N | O | 1-2 | 4-Br, 6-F | $CH_2OCH_3$ | J1 |
| 97 | N | O | 1-2 | 4-Cl, 6-F | $CH_2OCH_2CCH$ | J1 |
| 98 | N | O | 1-2 | 4-Br, 6-F | $NH_2$ | J1 |
| 99 | N | O | 1-2 | 4-Br, 6-F | phenoxymethyl | J1 |
| 100 | N | O | 1-2 | 4-Br, 6-F | $N(COCH_3)_2$ | J1 |
| 101 | N | O | 1-2 | 4-Br, 6-F | $CH_2OCOCH_3$ | J1 |
| 102 | N | O | 1-2 | 4-Br, 6-F | 4-chlorophenoxymethyl | J1 |
| 103 | N | O | 1-2 | 4-Br, 6-F | $CH(Ph)OCOCH_3$ | J1 |
| 104 | N | O | 1-2 | 4-Br, 6-F | $C(CH_3)_2OCOCH_3$ | J1 |
| 105 | N | O | 1-2 | 4-Br, 6-F | $CO_2H$ | J1 |
| 106 | N | O | 1-2 | 4-Br, 6-F | $OCH_2CCH$ | J1 |
| 107 | N | O | 1-2 | 4-Br, 6-F | $OCH(CH_3)_2$ | J1 |
| 108 | N | O | 1-2 | 4-Br, 6-F | $NHSO_2CH_3$ | J1 |
| 109 | N | O | 1-2 | 4-Br, 6-F | $OCH_3$ | J1 |
| 110 | N | O | 1-2 | 4-Br, 6-F | $OCH_2CH=CH_2$ | J1 |
| 111 | N | O | 1-2 | 4-Cl, 6-F | $(CH_3)(CN)OH$ | J1 |
| 112 | N | O | 1-2 | 4-Cl, 6-F | $CH_3$ | J2 |
| 113 | N | O | 1-2 | 4-Cl, 6-F | $n-C_3H_7$ | J2 |
| 114 | N | O | 1-2 | 4-Cl, 6-F | $i-C_3H_7$ | J2 |
| 115 | N | O | 1-2 | 4-Cl, 6-F | $t-C_4H_9$ | J2 |
| 116 | N | O | 1-2 | 4-Cl, 6-F | $C_2H_5$ | J2 |
| 117 | N | O | 1-2 | 4-Cl, 6-F | $CH_2CO_2CH_3$ | J2 |
| 118 | N | O | 1-2 | 4-Cl, 6-F | phenoxymethyl | J2 |
| 119 | N | O | 1-2 | 4-Cl, 6-F | $CONHCH_3$ | J2 |
| 120 | N | O | 1-2 | 4-Cl, 6-F | $CON(CH_3)_2$ | J2 |
| 121 | N | O | 1-2 | 4-Cl, 6-F | $CO_2CH_3$ | J2 |
| 122 | N | O | 1-2 | 4-Cl, 6-F | Phenyl | J2 |
| 123 | N | O | 1-2 | 4-Cl, 6-F | $SCH_3$ | J2 |
| 124 | N | O | 1-2 | 4-Cl, 6-F | $CH_2OCH_3$ | J2 |
| 125 | N | O | 1-2 | 4-Cl, 6-F | Benzyl | J2 |
| 126 | N | O | 1-2 | 4-Cl, 6-F | 4-chlorophenylmethyl | J2 |
| 127 | N | O | 1-2 | 4-Cl, 6-F | $SO_2CH_3$ | J2 |

TABLE 2-continued

| | | | | | | |
|---|---|---|---|---|---|---|
| 128 | N | O | 1-2 | 4-Cl, 6-F | $CF_3$ | J2 |
| 129 | N | O | 1-2 | 4-Cl, 6-F | $C(CH_3)_2OCO_2CH_3$ | J2 |
| 130 | N | O | 1-2 | 4-Cl, 6-F | $C(CH_3)_2CH_2OH$ | J2 |
| 131 | N | O | 1-2 | 4-Cl, 6-F | $CH_3$ | J3 |
| 132 | N | O | 1-2 | 4-Cl, 6-F | $n-C_3H_7$ | J3 |
| 133 | N | O | 1-2 | 4-Cl, 6-F | $i-C_3H_7$ | J3 |
| 134 | N | O | 1-2 | 4-Cl, 6-F | $t-C_4H_9$ | J3 |
| 135 | N | O | 1-2 | 4-Cl, 6-F | $CH_2OH$ | J3 |
| 136 | N | O | 1-2 | 4-Cl, 6-F | $CH_2CH_2OH$ | J3 |
| 137 | N | O | 1-2 | 4-Cl, 6-F | $C(CH_3)_2OH$ | J3 |
| 138 | N | O | 1-2 | 4-Cl, 6-F | $CONHCH_3$ | J3 |
| 139 | N | O | 1-2 | 4-Cl, 6-F | $CON(CH_3)_2$ | J3 |
| 140 | N | O | 1-2 | 4-Cl, 6-F | $CO_2CH_3$ | J3 |
| 141 | N | O | 1-2 | 4-Cl, 6-F | Phenyl | J3 |
| 142 | N | O | 1-2 | 4-Cl, 6-F | $SCH_3$ | J3 |
| 143 | N | O | 1-2 | 4-Cl, 6-F | $CH_2OCH_3$ | J3 |
| 144 | N | O | 1-2 | 4-Cl, 6-F | Benzyl | J3 |
| 145 | N | O | 1-2 | 4-Cl, 6-F | 4-chlorophenylmethyl | J3 |
| 146 | N | O | 1-2 | 4-Cl, 6-F | $SO_2CH_3$ | J3 |
| 147 | N | O | 1-2 | 4-Cl, 6-F | $CF_3$ | J3 |
| 148 | N | O | 1-2 | 4-Cl, 6-F | $C(CH_3)_2OCO_2CH_3$ | J3 |
| 149 | N | O | 1-2 | 4-Cl, 6-F | $C(CH_3)_2CH_2OH$ | J3 |
| 150 | N | O | 1-2 | 4-Cl, 6-F | $C(CH_3)_2CH_2OCH_3$ | J3 |
| 151 | N | O | 1-2 | 4-Cl, 6-F | $C_2H_5$ | J3 |
| 152 | N | O | 1-2 | 4-Cl, 6-F | $CO_2Na$ | J3 |
| 153 | N | O | 1-2 | 4-Cl, 6-F | $CONHSO_2CH_3$ | J3 |
| 154 | N | O | 1-2 | 4-Cl, 6-F | $OCH_2CO_2CH_3$ | J3 |
| 155 | N | O | 1-2 | 4-Cl, 6-F | $OCH(CH_3)CO_2CH_3$ | J3 |
| 156 | N | O | 1-2 | 4-Cl, 6-F | $OCH_2CH=CH_2$ | J3 |
| 157 | N | O | 1-2 | 4-Cl, 6-F | $OCH_2CCH$ | J3 |
| 158 | N | O | 1-2 | 4-Cl, 6-F | OH | J3 |
| 159 | N | O | 1-2 | 4-Cl, 6-F | $OCH_3$ | J3 |
| 160 | N | O | 1-2 | 4-Cl, 6-F | $OCH(CH_3)_2$ | J3 |
| 161 | N | O | 1-2 | 4-Cl, 6-F | $CH_3$ | J4 |
| 162 | N | O | 1-2 | 4-Cl, 6-F | $n-C_3H_7$ | J4 |
| 163 | N | O | 1-2 | 4-Cl, 6-F | $i-C_3H_7$ | J4 |
| 164 | N | O | 1-2 | 4-Cl, 6-F | $t-C_4H_9$ | J4 |
| 165 | N | O | 1-2 | 4-Cl, 6-F | $CH_2OH$ | J4 |
| 166 | N | O | 1-2 | 4-Cl, 6-F | $CH_2CH_2OH$ | J4 |
| 167 | N | O | 1-2 | 4-Cl, 6-F | $C(CH_3)_2OH$ | J4 |
| 168 | N | O | 1-2 | 4-Cl, 6-F | $CONHCH_3$ | J4 |
| 169 | N | O | 1-2 | 4-Cl, 6-F | $CON(CH_3)_2$ | J4 |
| 170 | N | O | 1-2 | 4-Cl, 6-F | $CO_2CH_3$ | J4 |
| 171 | N | O | 1-2 | 4-Cl, 6-F | Phenyl | J4 |
| 172 | N | O | 1-2 | 4-Cl, 6-F | $SCH_3$ | J4 |
| 173 | N | O | 1-2 | 4-Cl, 6-F | $CH_2OCH_3$ | J4 |
| 174 | N | O | 1-2 | 4-Cl, 6-F | Benzyl | J4 |
| 175 | N | O | 1-2 | 4-Cl, 6-F | 4-chlorophenylmethyl | J4 |
| 176 | N | O | 1-2 | 4-Cl, 6-F | $SO_2CH_3$ | J4 |
| 177 | N | O | 1-2 | 4-Cl, 6-F | $CF_3$ | J4 |
| 178 | N | O | 1-2 | 4-Cl, 6-F | $C(CH_3)_2OCO_2CH_3$ | J4 |
| 179 | N | O | 1-2 | 4-Cl, 6-F | $C(CH_3)_2CH_2OH$ | J4 |
| 180 | N | O | 1-2 | 4-Cl, 6-F | $C(CH_3)_2CH_2OCH_3$ | J4 |
| 181 | N | O | 1-2 | 4-Cl, 6-F | $C_2H_5$ | J4 |
| 182 | N | O | 1-2 | 4-Cl, 6-F | $CO_2Na$ | J4 |
| 183 | N | O | 1-2 | 4-Cl, 6-F | $CONHSO_2CH_3$ | J4 |
| 184 | N | O | 1-2 | 4-Cl, 6-F | $OCH_2CO_2CH_3$ | J4 |
| 185 | N | O | 1-2 | 4-Cl, 6-F | $OCH(CH_3)CO_2CH_3$ | J4 |
| 186 | N | O | 1-2 | 4-Cl, 6-F | $OCH_2CH=CH_2$ | J4 |
| 187 | N | O | 1-2 | 4-Cl, 6-F | $OCH_2C\equiv CH$ | J4 |
| 188 | N | O | 1-2 | 4-Cl, 6-F | OH | J4 |
| 189 | N | O | 1-2 | 4-Cl, 6-F | $OCH_3$ | J4 |
| 190 | N | O | 1-2 | 4-Cl, 6-F | $OCH(CH_3)_2$ | J4 |
| 191 | N | O | 1-2 | 4-Cl, 6-F | $CH_3$ | J5 |
| 192 | N | O | 1-2 | 4-Cl, 6-F | $n-C_3H_7$ | J5 |
| 193 | N | O | 1-2 | 4-Cl, 6-F | $i-C_3H_7$ | J5 |
| 194 | N | O | 1-2 | 4-Cl, 6-F | $t-C_4H_9$ | J5 |
| 195 | N | O | 1-2 | 4-Cl, 6-F | $CH_2OH$ | J5 |
| 196 | N | O | 1-2 | 4-Cl, 6-F | $CH_2CH_2OH$ | J5 |
| 197 | N | O | 1-2 | 4-Cl, 6-F | $C(CH_3)_2OH$ | J5 |
| 198 | N | O | 1-2 | 4-Cl, 6-F | $CONHCH_3$ | J5 |
| 199 | N | O | 1-2 | 4-Cl, 6-F | $CON(CH_3)_2$ | J5 |
| 200 | N | O | 1-2 | 4-Cl, 6-F | $CO_2CH_3$ | J5 |
| 201 | N | O | 1-2 | 4-Cl, 6-F | Phenyl | J5 |
| 202 | N | O | 1-2 | 4-Cl, 6-F | $SCH_3$ | J5 |
| 203 | N | O | 1-2 | 4-Cl, 6-F | $CH_2OCH_3$ | J5 |
| 204 | N | O | 1-2 | 4-Cl, 6-F | Benzyl | J5 |
| 205 | N | O | 1-2 | 4-Cl, 6-F | 4-chlorophenylmethyl | J5 |
| 206 | N | O | 1-2 | 4-Cl, 6-F | $SO_2CH_3$ | J5 |

TABLE 2-continued

| | | | | | | |
|---|---|---|---|---|---|---|
| 207 | N | O | 1-2 | 4-Cl, 6-F | $CF_3$ | J5 |
| 208 | N | O | 1-2 | 4-Cl, 6-F | $C(CH_3)_2OCO_2CH_3$ | J5 |
| 209 | N | O | 1-2 | 4-Cl, 6-F | $C(CH_3)_2CH_2OH$ | J5 |
| 210 | N | O | 1-2 | 4-Cl, 6-F | $C(CH_3)_2CH_2OCH_3$ | J5 |
| 211 | N | O | 1-2 | 4-Cl, 6-F | $C_2H_5$ | J5 |
| 212 | N | O | 1-2 | 4-Cl, 6-F | $CO_2Na$ | J5 |
| 213 | N | O | 1-2 | 4-Cl, 6-F | $CONHSO_2CH_3$ | J5 |
| 214 | N | O | 1-2 | 4-Cl, 6-F | $OCH_2CO_2CH_3$ | J5 |
| 215 | N | O | 1-2 | 4-Cl, 6-F | $OCH(CH_3)CO_2CH_3$ | J5 |
| 216 | N | O | 1-2 | 4-Cl, 6-F | $OCH_2CH=CH_2$ | J5 |
| 217 | N | O | 1-2 | 4-Cl, 6-F | $OCH_2CCH$ | J5 |
| 218 | N | O | 1-2 | 4-Cl, 6-F | OH | J5 |
| 219 | N | O | 1-2 | 4-Cl, 6-F | $OCH_3$ | J5 |
| 220 | N | O | 1-2 | 4-Cl, 6-F | $OCH(CH_3)_2$ | J5 |
| 221 | O | CH | 2-3 | 4-Cl | $CH_3$ | J1 |
| 222 | O | CH | 2-3 | 4-Cl, 6-F | $CH_3$ | J1 |
| 223 | O | CH | 2-3 | 4-Cl, 6-F | n-propyl | J1 |
| 224 | O | CH | 2-3 | 4-Cl, 6-F | isopropyl | J1 |
| 225 | O | CH | 2-3 | 4-Cl | n-butyl | J1 |
| 226 | O | CH | 2-3 | 4-Cl | t-butyl | J1 |
| 227 | O | CH | 2-3 | 4-Cl, 6-F | t-butyl | J1 |
| 228 | O | CH | 2-3 | 4,6-$F_2$ | t-butyl | J1 |
| 229 | O | CH | 2-3 | 4-Cl, 6-F | $CH(CH_3)C_3H_7$ | J1 |
| 230 | O | CH | 2-3 | 4-Cl, 6-F | $CH=CH_2$ | J1 |
| 231 | O | CH | 2-3 | 4-Cl, 6-F | $C(CH_3)=CH_2$ | J1 |
| 232 | O | CH | 2-3 | 4-Cl | $CH_2Br$ | J1 |
| 233 | O | CH | 2-3 | 4-Cl | $CHBr_2$ | J1 |
| 234 | O | CH | 2-3 | 4-Cl, 6-F | $CH(Cl)CH_3$ | J1 |
| 235 | O | CH | 2-3 | 4-Cl, 6-F | $CH(F)CH_3$ | J1 |
| 236 | O | CH | 2-3 | 4-Cl, 6-F | $CH_2CH_2Cl$ | J1 |
| 237 | O | CH | 2-3 | 4-Cl, 6-F | $CH_2CH_2F$ | J1 |
| 238 | O | CH | 2-3 | 4-Cl | $CH_2OH$ | J1 |
| 239 | O | CH | 2-3 | 4-Cl, 6-F | $CH_2CH_2OH$ | J1 |
| 240 | O | CH | 2-3 | 4-Cl, 6-F | $CH(CH_3)OH$ | J1 |
| 241 | O | CH | 2-3 | 4-Cl | $C(CH_3)_2OH$ | J1 |
| 242 | O | CH | 2-3 | 4-Cl, 6-F | $C(CH_3)_2OH$ | J1 |
| 243 | O | CH | 2-3 | 4-Cl, 6-F | $CH_2CH(CH_3)OH$ | J1 |
| 244 | O | CH | 2-3 | 4-Cl, 6-F | $CH(CH_3)OC(CH_3)_3$ | J1 |
| 245 | O | CH | 2-3 | 4-Cl, 6-F | $CH(OC_2H_5)_2$ | J1 |
| 246 | O | CH | 2-3 | 4-Cl, 6-F | $CH(CH_3)OCOCH_3$ | J1 |
| 247 | O | CH | 2-3 | 4-Cl, 6-F | $CH(CH_3)OCOCH(CH_3)_2$ | J1 |
| 248 | O | CH | 2-3 | 4-Cl, 6-F | $CH(CH_3)OCOPh$ | J1 |
| 249 | O | CH | 2-3 | 4-Cl, 6-F | $CH(CH_3)OCONHCH_3$ | J1 |
| 250 | O | CH | 2-3 | 4-Cl, 6-F | $CH(CH_3)OCONHCH_2Ph$ | J1 |
| 251 | O | CH | 2-3 | 4-Cl | $C(CH_3)_2OCH_3$ | J1 |
| 252 | O | CH | 2-3 | 4-Cl, 6-F | $C(CH_3)_2OCH_2OCH_3$ | J1 |
| 253 | O | CH | 2-3 | 4-Cl, 6-F | $C(CH_3)_2OCOCH_3$ | J1 |
| 254 | O | CH | 2-3 | 4-Cl, 6-F | $C(CH_3)_2NH_2$ | J1 |
| 255 | O | CH | 2-3 | 4-Cl, 6-F | $C(CH_3)_2NHSO_2CH_3$ | J1 |
| 256 | O | CH | 2-3 | 4-Cl, 6-F | $CH_2CH_2CH_2CN$ | J1 |
| 257 | O | CH | 2-3 | 4-Cl | $CH_2N(C_2H_5)_2$ | J1 |
| 258 | O | CH | 2-3 | 4-Cl | $CH=NOH$ | J1 |
| 259 | O | CH | 2-3 | 4-Cl | $CH=NOCH_3$ | J1 |
| 260 | O | CH | 2-3 | 4-Cl, 6-F | $CH_2CH_2OCOCH_3$ | J1 |
| 261 | O | CH | 2-3 | 4-Cl, 6-F | $CH_2CH_2OCONHCH_3$ | J1 |
| 262 | O | CH | 2-3 | 4-Cl, 6-F | $CH_2CH_2CO_2H$ | J1 |
| 263 | O | CH | 2-3 | 4-Cl, 6-F | $CH_2CH_2CO_2CH_3$ | J1 |
| 264 | O | CH | 2-3 | 4-Cl | Phenyl | J1 |
| 265 | O | CH | 2-3 | 4-Cl | CHO | J1 |
| 266 | O | CH | 2-3 | 4-Cl | $CO_2H$ | J1 |
| 267 | O | CH | 2-3 | H | $CO_2C_2H_5$ | J1 |
| 268 | O | CH | 2-3 | 4-Cl | $CO_2C_2H_5$ | J1 |
| 269 | O | CH | 2-3 | 4-Cl | $CONH_2$ | J1 |
| 270 | O | CH | 2-3 | 4-Cl | $CONHCH_3$ | J1 |
| 271 | O | CH | 2-3 | 4-Cl | $CON(CH_3)_2$ | J1 |
| 272 | O | CH | 2-3 | 4-Cl | $NHCO_2C(CH_3)_3$ | J1 |
| 273 | O | CH | 2-3 | 4-Cl, 6-F | $CONH_2$ | J1 |
| 274 | O | CH | 2-3 | 4-Cl, 6-F | $CONH(CH_3)$ | J1 |
| 275 | O | CH | 2-3 | 4-Cl, 6-F | $CON(CH_3)_2$ | J1 |
| 276 | O | CH | 2-3 | 4-Cl, 6-F | $CO_2H$ | J1 |
| 277 | O | CH | 2-3 | 4-Cl, 6-F | $CO_2CH_3$ | J1 |
| 278 | O | CH | 2-3 | 4-Cl, 6-F | $CH_2OH$ | J1 |
| 279 | O | CH | 2-3 | 4-Cl, 6-F | 3,4-dimethoxyphenyl | J1 |
| 280 | O | CH | 2-3 | 4-Cl, 6-F | Phenyl | J1 |
| 281 | O | CH | 2-3 | 4-Cl, 6-F | $CH_3$ | J2 |
| 282 | O | CH | 2-3 | 4-Cl, 6-F | n-propyl | J2 |
| 283 | O | CH | 2-3 | 4-Cl, 6-F | isopropyl | J2 |
| 284 | O | CH | 2-3 | 4-Cl, 6-F | t-butyl | J2 |
| 285 | O | CH | 2-3 | 4-Cl, 6-F | $CH(CH_3)C_3H_7$ | J2 |

TABLE 2-continued

| | | | | | | |
|---|---|---|---|---|---|---|
| 286 | O | CH | 2-3 | 4-Cl, 6-F | CH=CH$_2$ | J2 |
| 287 | O | CH | 2-3 | 4-Cl, 6-F | C(CH$_3$)=CH$_2$ | J2 |
| 288 | O | CH | 2-3 | 4-Cl, 6-F | CH(Cl)CH$_3$ | J2 |
| 289 | O | CH | 2-3 | 4-Cl, 6-F | CH(F)CH$_3$ | J2 |
| 290 | O | CH | 2-3 | 4-Cl, 6-F | CH$_2$CH$_2$Cl | J2 |
| 291 | O | CH | 2-3 | 4-Cl, 6-F | CH$_2$CH$_2$F | J2 |
| 292 | O | CH | 2-3 | 4-Cl, 6-F | CH$_2$CH$_2$OH | J2 |
| 293 | O | CH | 2-3 | 4-Cl, 6-F | CH(CH$_3$)OH | J2 |
| 294 | O | CH | 2-3 | 4-Cl, 6-F | C(CH$_3$)$_2$OH | J2 |
| 295 | O | CH | 2-3 | 4-Cl, 6-F | CH$_2$CH(CH$_3$)OH | J2 |
| 296 | O | CH | 2-3 | 4-Cl, 6-F | CH(CH$_3$)OC(CH$_3$)$_3$ | J2 |
| 297 | O | CH | 2-3 | 4-Cl, 6-F | CH(OC$_2$H$_5$)$_2$ | J2 |
| 298 | O | CH | 2-3 | 4-Cl, 6-F | CH(CH$_3$)OCOCH$_3$ | J2 |
| 299 | O | CH | 2-3 | 4-Cl, 6-F | CH(CH$_3$)OCOCH(CH$_3$)$_2$ | J2 |
| 300 | O | CH | 2-3 | 4-Cl, 6-F | CH(CH$_3$)OCOPh | J2 |
| 301 | O | CH | 2-3 | 4-Cl, 6-F | CH(CH$_3$)OCONHCH$_3$ | J2 |
| 302 | O | CH | 2-3 | 4-Cl, 6-F | CH(CH$_3$)OCONHCH$_2$Ph | J2 |
| 303 | O | CH | 2-3 | 4-Cl, 6-F | C(CH$_3$)$_2$OCH$_2$OCH$_3$ | J2 |
| 304 | O | CH | 2-3 | 4-Cl, 6-F | C(CH$_3$)$_2$OCOCH$_3$ | J2 |
| 305 | O | CH | 2-3 | 4-Cl, 6-F | C(CH$_3$)$_2$NH$_2$ | J2 |
| 306 | O | CH | 2-3 | 4-Cl, 6-F | C(CH$_3$)$_2$NHSO$_2$CH$_3$ | J2 |
| 307 | O | CH | 2-3 | 4-Cl, 6-F | CH$_2$CH$_2$CH$_2$CN | J2 |
| 308 | O | CH | 2-3 | 4-Cl, 6-F | CH$_2$CH$_2$OCOCH$_3$ | J2 |
| 309 | O | CH | 2-3 | 4-Cl, 6-F | CH$_2$CH$_2$OCONHCH$_3$ | J2 |
| 310 | O | CH | 2-3 | 4-Cl, 6-F | CH$_2$CH$_2$CO$_2$H | J2 |
| 311 | O | CH | 2-3 | 4-Cl, 6-F | CH$_2$CH$_2$CO$_2$CH$_3$ | J2 |
| 312 | O | CH | 2-3 | 4-Cl, 6-F | CONH$_2$ | J2 |
| 313 | O | CH | 2-3 | 4-Cl, 6-F | CONH(CH$_3$) | J2 |
| 314 | O | CH | 2-3 | 4-Cl, 6-F | CON(CH$_3$)$_2$ | J2 |
| 315 | O | CH | 2-3 | 4-Cl, 6-F | CO$_2$H | J2 |
| 316 | O | CH | 2-3 | 4-Cl, 6-F | CO$_2$CH$_3$ | J2 |
| 317 | O | CH | 2-3 | 4-Cl, 6-F | CH$_2$OH | J2 |
| 318 | O | CH | 2-3 | 4-Cl, 6-F | 3,4-dimethoxyphenyl | J2 |
| 319 | O | CH | 2-3 | 4-Cl, 6-F | Phenyl | J2 |
| 320 | O | CH | 2-3 | 4-Cl, 6-F | CH$_3$ | J3 |
| 321 | O | CH | 2-3 | 4-Cl, 6-F | C$_2$H$_5$ | J3 |
| 322 | O | CH | 2-3 | 4-Cl, 6-F | CH(Cl)CH$_3$ | J3 |
| 323 | O | CH | 2-3 | 4-Cl, 6-F | CH(F)CH$_3$ | J3 |
| 324 | O | CH | 2-3 | 4-Cl, 6-F | CH$_2$CH$_2$Cl | J3 |
| 325 | O | CH | 2-3 | 4-Cl, 6-F | CH$_2$CH$_2$F | J3 |
| 326 | O | CH | 2-3 | 4-Cl, 6-F | CH$_2$CH$_2$OH | J3 |
| 327 | O | CH | 2-3 | 4-Cl, 6-F | CH(CH$_3$)OH | J3 |
| 328 | O | CH | 2-3 | 4-Cl, 6-F | C(CH$_3$)$_2$OH | J3 |
| 329 | O | CH | 2-3 | 4-Cl, 6-F | C(CH$_3$)$_2$OCH$_2$OCH$_3$ | J3 |
| 330 | O | CH | 2-3 | 4-Cl, 6-F | C(CH$_3$)$_2$NHSO$_2$CH$_3$ | J3 |
| 331 | O | CH | 2-3 | 4-Cl, 6-F | CH$_2$CH$_2$CH$_2$CN | J3 |
| 332 | O | CH | 2-3 | 4-Cl, 6-F | CH$_2$CH$_2$CO$_2$CH$_3$ | J3 |
| 333 | O | CH | 2-3 | 4-Cl, 6-F | CON(CH$_3$)$_2$ | J3 |
| 334 | O | CH | 2-3 | 4-Cl, 6-F | CH$_3$ | J4 |
| 335 | O | CH | 2-3 | 4-Cl, 6-F | C$_2$H$_5$ | J4 |
| 336 | O | CH | 2-3 | 4-Cl, 6-F | CH(Cl)CH$_3$ | J4 |
| 337 | O | CH | 2-3 | 4-Cl, 6-F | CH(F)CH$_3$ | J4 |
| 338 | O | CH | 2-3 | 4-Cl, 6-F | CH$_2$CH$_2$Cl | J4 |
| 339 | O | CH | 2-3 | 4-Cl, 6-F | CH$_2$CH$_2$F | J4 |
| 340 | O | CH | 2-3 | 4-Cl, 6-F | CH$_2$CH$_2$OH | J4 |
| 341 | O | CH | 2-3 | 4-Cl, 6-F | CH(CH$_3$)OH | J4 |
| 342 | O | CH | 2-3 | 4-Cl, 6-F | C(CH$_3$)$_2$OH | J4 |
| 343 | O | CH | 2-3 | 4-Cl, 6-F | C(CH$_3$)$_2$OCH$_2$OCH$_3$ | J4 |
| 344 | O | CH | 2-3 | 4-Cl, 6-F | C(CH$_3$)$_2$NHSO$_2$CH$_3$ | J4 |
| 345 | O | CH | 2-3 | 4-Cl, 6-F | CH$_2$CH$_2$CH$_2$CN | J4 |
| 346 | O | CH | 2-3 | 4-Cl, 6-F | CH$_2$CH$_2$CO$_2$CH$_3$ | J4 |
| 347 | O | CH | 2-3 | 4-Cl, 6-F | CON(CH$_3$)$_2$ | J4 |
| 348 | O | CH | 2-3 | 4-Cl, 6-F | CH$_3$ | J5 |
| 349 | O | CH | 2-3 | 4-Cl, 6-F | C$_2$H$_5$ | J5 |
| 350 | O | CH | 2-3 | 4-Cl, 6-F | CH(Cl)CH$_3$ | J5 |
| 351 | O | CH | 2-3 | 4-Cl, 6-F | CH(F)CH$_3$ | J5 |
| 352 | O | CH | 2-3 | 4-Cl, 6-F | CH$_2$CH$_2$Cl | J5 |
| 353 | O | CH | 2-3 | 4-Cl, 6-F | CH$_2$CH$_2$F | J5 |
| 354 | O | CH | 2-3 | 4-Cl, 6-F | CH$_2$CH$_2$OH | J5 |
| 355 | O | CH | 2-3 | 4-Cl, 6-F | CH(CH$_3$)OH | J5 |
| 356 | O | CH | 2-3 | 4-Cl, 6-F | C(CH$_3$)$_2$OH | J5 |
| 357 | O | CH | 2-3 | 4-Cl, 6-F | C(CH$_3$)$_2$OCH$_2$OCH$_3$ | J5 |
| 358 | O | CH | 2-3 | 4-Cl, 6-F | C(CH$_3$)$_2$NHSO$_2$CH$_3$ | J5 |
| 359 | O | CH | 2-3 | 4-Cl, 6-F | CH$_2$CH$_2$CH$_2$CN | J5 |
| 360 | O | CH | 2-3 | 4-Cl, 6-F | CH$_2$CH$_2$CO$_2$CH$_3$ | J5 |
| 361 | O | CH | 2-3 | 4-Cl, 6-F | CON(CH$_3$)$_2$ | J5 |
| 362 | NH | N | 2-3 | 4-Cl, 6-F | H | J1 |
| 363 | NH | N | 2-3 | 4-Cl, 6-F | CH$_3$ | J1 |
| 364 | NH | N | 2-3 | 4-Cl, 6-F | CHF$_2$ | J1 |

TABLE 2-continued

| | | | | | | |
|---|---|---|---|---|---|---|
| 365 | NH | N | 2-3 | 4-Cl, 6-F | $CF_3$ | J1 |
| 366 | NH | N | 2-3 | 4-Cl, 6-F | $CClF_2$ | J1 |
| 367 | NH | N | 2-3 | 4-Cl, 6-F | $C_2H_5$ | J1 |
| 368 | NH | N | 2-3 | 4-Cl, 6-F | $i\text{-}C_3H_7$ | J1 |
| 369 | NH | N | 2-3 | 4-Cl, 6-F | $t\text{-}C_4H_9$ | J1 |
| 370 | NH | N | 2-3 | 4-Cl, 6-F | $CH_2OCH_3$ | J1 |
| 371 | NH | N | 2-3 | 4-Cl, 6-F | $C(CH_3)_2OC(O)CH_3$ | J1 |
| 372 | NH | N | 2-3 | 4-Cl, 6-F | $C_2H_4CO_2C_2H_5$ | J1 |
| 373 | NH | N | 2-3 | 4-Cl, 6-F | Cyclohexyl | J1 |
| 374 | NH | N | 2-3 | 4-Cl, 6-F | Adamantyl | J1 |
| 375 | NH | N | 2-3 | 4-Cl, 6-F | Phenyl | J1 |
| 376 | NH | N | 2-3 | 4-Cl, 6-F | Benzyl | J1 |
| 377 | NH | N | 2-3 | 4-Cl, 6-F | $CH(CH_3)C_6H_5$ | J1 |
| 378 | NH | N | 2-3 | 4-Cl, 6-F | $CH_2OC_6H_5$ | J1 |
| 379 | NH | N | 2-3 | 4-Cl, 6-F | $C_2H_4C_8H_5$ | J1 |
| 380 | NH | N | 2-3 | 4-Cl, 6-F | $C_3H_6C_6H_5$ | J1 |
| 381 | NH | N | 2-3 | 4-Cl, 6-F | 2-chlorophenylmethyl | J1 |
| 382 | NH | N | 2-3 | 4-Cl, 6-F | 3-chlorophenylmethyl | J1 |
| 383 | NH | N | 2-3 | 4-Cl, 6-F | 4-chlorophenylmethyl | J1 |
| 384 | NH | N | 2-3 | 4-Cl, 6-F | $CF_2CF_3$ | J1 |
| 385 | NH | N | 2-3 | 4-Cl, 6-F | Furan-2-yl | J1 |
| 386 | NH | N | 2-3 | 4-Cl, 6-F | $CH_2Cl$ | J1 |
| 387 | NH | N | 2-3 | 4-Cl, 6-F | $C(CH_3)_2CH_2Cl$ | J1 |
| 388 | NH | N | 2-3 | 4-Cl, 6-F | $OC_2H_5$ | J1 |
| 389 | N | NH | 1-2 | 4-Cl, 6-F | $CH_3$ | J1 |
| 390 | N | NH | 1-2 | 4-Cl, 6-F | $C_2H_5$ | J1 |
| 391 | N | NH | 1-2 | 4-Cl, 6-F | isopropyl | J1 |
| 392 | N | NH | 1-2 | 4-Cl, 6-F | t-butyl | J1 |
| 393 | N | NH | 1-2 | 4-Cl, 6-F | $CF_3$ | J1 |
| 394 | N | NH | 1-2 | 4-Cl, 6-F | $CF_2CF_3$ | J1 |
| 395 | N | $NCH_3$ | 1-2 | 4-Cl, 6-F | $CH_3$ | J1 |
| 396 | N | $NCH_3$ | 1-2 | 4-Cl, 6-F | $C_2H_5$ | J1 |
| 397 | N | $NCH_3$ | 1-2 | 4-Cl, 6-F | isopropyl | J1 |
| 398 | N | $NCH_3$ | 1-2 | 4-Cl, 6-F | t-butyl | J1 |
| 399 | N | $NCH_3$ | 1-2 | 4-Cl, 6-F | $CF_3$ | J1 |
| 400 | N | $NCH_3$ | 1-2 | 4-Cl, 6-F | $CF_2CF_3$ | J1 |
| 401 | N | $NCH_3$ | 1-2 | 4-Cl, 6-F | $CO_2CH_2CH_3$ | J1 |
| 402 | N | $NC_2H_5$ | 1-2 | 4-Cl, 6-F | $CH_3$ | J1 |
| 403 | N | $NC_2H_5$ | 1-2 | 4-Cl, 6-F | $C_2H_5$ | J1 |
| 404 | NH | NH | — | $4\text{-}NO_2$, 6-F | $CF_3$ | J1 |
| 405 | $N^-H_3N^+CH(CH_3)_2$ | N | 2-3 | 4-Cl, 6-F | $CH_3$ | J1 |
| 406 | $NCH_3$ | N | 2-3 | 4-Cl, 6-F | $CF_3$ | J1 |
| 407 | $NCH_3$ | $NC_2H_5$ | 1-2 | 4-Cl, 6-F | isopropyl | J1 |
| 408 | N | $NC_2H_5$ | 1-2 | 4-Cl, 6-F | t-butyl | J1 |
| 409 | N | $NC_2H_5$ | 1-2 | 4-Cl, 6-F | $CF_3$ | J1 |
| 410 | N | $NC_2H_5$ | 1-2 | 4-Cl, 6-F | $CF_2CF_3$ | J1 |
| 411 | N | $NC_4H_9$ | 1-2 | 4-Cl, 6-F | $CH_3$ | J1 |
| 412 | N | $NC_4H_9$ | 1-2 | 4-Cl, 6-F | $C_2H_5$ | J1 |
| 413 | N | $NC_4H_9$ | 1-2 | 4-Cl, 6-F | isopropyl | J1 |
| 414 | N | $NC_4H_9$ | 1-2 | 4-Cl, 6-F | t-butyl | J1 |
| 415 | N | $NC_4H_9$ | 1-2 | 4-Cl, 6-F | $CF_3$ | J1 |
| 416 | N | $NC_4H_9$ | 1-2 | 4-Cl, 6-F | $CF_2CF_3$ | J1 |
| 417 | N | $NCH_2OCH_3$ | 1-2 | 4-Cl, 6-F | $CH_3$ | J1 |
| 418 | N | $NCH_2OCH_3$ | 1-2 | 4-Cl, 6-F | $C_2H_5$ | J1 |
| 419 | N | $NCH_2OCH_3$ | 1-2 | 4-Cl, 6-F | isopropyl | J1 |
| 420 | N | $NCH_2OCH_3$ | 1-2 | 4-Cl, 6-F | t-butyl | J1 |
| 421 | N | $NCH_2OCH_3$ | 1-2 | 4-Cl, 6-F | $CF_3$ | J1 |
| 422 | N | $NCH_2OCH_3$ | 1-2 | 4-Cl, 6-F | $CF_2CF_3$ | J1 |
| 423 | N | $NCO_2CH_3$ | 1-2 | 4-Cl, 6-F | $CH_3$ | J1 |
| 424 | N | $NCO_2CH_3$ | 1-2 | 4-Cl, 6-F | $C_2H_5$ | J1 |
| 425 | N | $NCO_2CH_3$ | 1-2 | 4-Cl, 6-F | isopropyl | J1 |
| 426 | N | $NCO_2CH_3$ | 1-2 | 4-Cl, 6-F | t-butyl | J1 |
| 427 | N | $NCO_2CH_3$ | 1-2 | 4-Cl, 6-F | $CF_3$ | J1 |
| 428 | N | $NCO_2CH_3$ | 1-2 | 4-Cl, 6-F | $CF_2CF_3$ | J1 |
| 429 | N | $NSO_2CH_3$ | 1-2 | 4-Cl, 6-F | $CH_3$ | J1 |
| 430 | N | $NSO_2CH_3$ | 1-2 | 4-Cl, 6-F | $C_2H_5$ | J1 |
| 431 | N | $NSO_2CH_3$ | 1-2 | 4-Cl, 6-F | isopropyl | J1 |
| 432 | N | $NSO_2CH_3$ | 1-2 | 4-Cl, 6-F | t-butyl | J1 |
| 433 | N | $NSO_2CH_3$ | 1-2 | 4-Cl, 6-F | $CF_3$ | J1 |
| 434 | N | $NSO_2CH_3$ | 1-2 | 4-Cl, 6-F | $CF_2CF_3$ | J1 |
| 435 | N | $NCH_2CHCH_2$ | 1-2 | 4-Cl, 6-F | $CH_3$ | J1 |
| 436 | N | $NCH_3CHCH_2$ | 1-2 | 4-Cl, 6-F | $C_2H_5$ | J1 |
| 437 | N | $NCH_2CHCH_2$ | 1-2 | 4-Cl, 6-F | isopropyl | J1 |
| 438 | N | $NCH_3CHCH_2$ | 1-2 | 4-Cl, 6-F | t-butyl | J1 |
| 439 | N | $NCH_2CHCH_2$ | 1-2 | 4-Cl, 6-F | $CF_3$ | J1 |
| 440 | N | $NCH_3CHCH_2$ | 1-2 | 4-Cl, 6-F | $CF_2CF_3$ | J1 |
| 441 | N | $NCH_2CCH$ | 1-2 | 4-Cl, 6-F | $CH_3$ | J1 |
| 442 | N | $NCH_2CCH$ | 1-2 | 4-Cl, 6-F | $C_2H_5$ | J1 |
| 443 | N | $NCH_2CCH$ | 1-2 | 4-Cl, 6-F | isopropyl | J1 |

TABLE 2-continued

| | | | | | | |
|---|---|---|---|---|---|---|
| 444 | N | NCH$_2$CCH | 1-2 | 4-Cl, 6-F | t-butyl | J1 |
| 445 | N | NCH$_2$CCH | 1-2 | 4-Cl, 6-F | CF$_3$ | J1 |
| 446 | N | NCH$_2$CCH | 1-2 | 4-Cl, 6-F | CF$_2$CF$_3$ | J1 |
| 447 | N | NCH$_2$CO$_2$Me | 1-2 | 4-Cl, 6-F | CH$_3$ | J1 |
| 448 | N | NCH$_2$CO$_2$Me | 1-2 | 4-Cl, 6-F | C$_2$H$_5$ | J1 |
| 449 | N | NCH$_2$CO$_2$Me | 1-2 | 4-Cl, 6-F | isopropyl | J1 |
| 450 | N | NCH$_2$CO$_2$Me | 1-2 | 4-Cl, 6-F | t-butyl | J1 |
| 451 | N | NCH$_2$CO$_2$Me | 1-2 | 4-Cl, 6-F | CF$_3$ | J1 |
| 452 | N | NCH$_2$CO$_2$Me | 1-2 | 4-Cl, 6-F | CF$_2$CF$_3$ | J1 |
| 453 | N | NCF$_3$ | 1-2 | 4-Cl, 6-F | CH$_3$ | J1 |
| 454 | N | NCF$_3$ | 1-2 | 4-Cl, 6-F | C$_2$H$_5$ | J1 |
| 455 | N | NCH$_2$CO$_2$Me | 1-2 | 4-Cl, 6-F | isopropyl | J1 |
| 456 | N | NCH$_2$CO$_2$Me | 1-2 | 4-Cl, 6-F | t-butyl | J1 |
| 457 | N | NCH$_2$CO$_2$Me | 1-2 | 4-Cl, 6-F | CF$_3$ | J1 |
| 458 | N | NCF$_3$ | 1-2 | 4-Cl, 6-F | CF$_2$CF$_3$ | J1 |
| 459 | NH | N | 2-3 | 4-Cl, 6-F | CH$_3$ | J2 |
| 460 | NH | N | 2-3 | 4-Cl, 6-F | C$_2$H$_5$ | J2 |
| 461 | NH | N | 2-3 | 4-Cl, 6-F | isopropyl | J2 |
| 462 | NH | N | 2-3 | 4-Cl, 6-F | t-butyl | J2 |
| 463 | NH | N | 2-3 | 4-Cl, 6-F | CF$_3$ | J2 |
| 464 | NH | N | 2-3 | 4-Cl, 6-F | CF$_2$CF$_3$ | J2 |
| 465 | NH | N | 2-3 | 4-Cl, 6-F | CH$_3$ | J3 |
| 466 | NH | N | 2-3 | 4-Cl, 6-F | C$_2$H$_5$ | J3 |
| 467 | NH | N | 2-3 | 4-Cl, 6-F | isopropyl | J3 |
| 468 | NH | N | 2-3 | 4-Cl, 6-F | t-butyl | J3 |
| 469 | NH | N | 2-3 | 4-Cl, 6-F | CF$_3$ | J3 |
| 470 | NH | N | 2-3 | 4-Cl, 6-F | CF$_2$CF$_3$ | J3 |
| 471 | NH | N | 2-3 | 4-Cl, 6-F | CH$_3$ | J4 |
| 472 | NH | N | 2-3 | 4-Cl, 6-F | C$_2$H$_5$ | J4 |
| 473 | NH | N | 2-3 | 4-Cl, 6-F | isopropyl | J4 |
| 474 | NH | N | 2-3 | 4-Cl, 6-F | t-butyl | J4 |
| 475 | NH | N | 2-3 | 4-Cl, 6-F | CF$_3$ | J4 |
| 476 | NH | N | 2-3 | 4-Cl, 6-F | CF$_2$CF$_3$ | J4 |
| 477 | NH | N | 2-3 | 4-Cl, 6-F | CH$_3$ | J5 |
| 478 | NH | N | 2-3 | 4-Cl, 6-F | C$_2$H$_5$ | J5 |
| 479 | NH | N | 2-3 | 4-Cl, 6-F | isopropyl | J5 |
| 480 | NH | N | 2-3 | 4-Cl, 6-F | t-butyl | J5 |
| 481 | NH | N | 2-3 | 4-Cl, 6-F | CF$_3$ | J5 |
| 482 | NH | N | 2-3 | 4-Cl, 6-F | CF$_2$CF$_3$ | J5 |
| 483 | NH | NH | 1-2 | 4-Cl, 6-F | CH$_3$ | J1 |
| 484 | CH | NH | 1-2 | 4-Cl, 6-F | n-C$_3$H$_7$ | J1 |
| 485 | CH | NH | 1-2 | 4-Cl, 6-F | i-C$_3$H$_7$ | J1 |
| 486 | CH | NH | 1-2 | 4-Cl, 6-F | t-C$_4$H$_9$ | J1 |
| 487 | CH | NH | 1-2 | 4-Cl, 6-F | CH$_2$OH | J1 |
| 488 | CH | NH | 1-2 | 4-Cl, 6-F | CH$_2$CH$_2$OH | J1 |
| 489 | CH | NH | 1-2 | 4-Cl, 6-F | C(CH$_3$)$_2$OH | J1 |
| 490 | CH | NH | 1-2 | 4-Cl, 6-F | CONHCH$_3$ | J1 |
| 491 | CH | NH | 1-2 | 4-Cl, 6-F | CON(CH$_3$)$_2$ | J1 |
| 492 | CH | NH | 1-2 | 4-Cl, 6-F | CO$_2$CH$_3$ | J1 |
| 493 | CH | NH | 1-2 | 4-Cl, 6-F | CO$_2$CH$_2$CH$_3$ | J1 |
| 494 | CH | NH | 1-2 | 4-Cl, 6-F | Phenyl | J1 |
| 495 | CH | NH | 1-2 | 4-Cl, 6-F | CF$_2$CF$_3$ | J1 |
| 496 | CH | NH | 1-2 | 4-Cl, 6-F | CH$_2$OCH$_3$ | J1 |
| 497 | CH | NH | 1-2 | 4-Cl, 6-F | Benzyl | J1 |
| 498 | CH | NH | 1-2 | 4-Cl, 6-F | 4-chlorophenylmethyl | J1 |
| 499 | CH | NH | 1-2 | 4-Cl, 6-F | SO$_2$CH$_3$ | J1 |
| 500 | CH | NH | 1-2 | 4-Cl, 6-F | CF$_3$ | J1 |
| 501 | CH | NH | 1-2 | 4-Cl, 6-F | C(CH$_3$)$_2$OCOCH$_3$ | J1 |
| 502 | CH | NH | 1-2 | 4-Cl, 6-F | C(CH$_3$)$_2$CH$_2$OH | J1 |
| 503 | CH | NH | 1-2 | 4-Cl, 6-F | C(CH$_3$)$_2$CH$_2$OCH$_3$ | J1 |
| 504 | CH | NH | 1-2 | 4-Cl, 6-F | C$_2$H$_5$ | J1 |
| 505 | CH | NH | 1-2 | 4-Cl, 6-F | CO$_2$Na | J1 |
| 506 | CH | NH | 1-2 | 4-Cl, 6-F | CONHSO$_2$CH$_3$ | J1 |
| 507 | CH | NH | 1-2 | 4-Cl, 6-F | CHFCH$_3$ | J1 |
| 508 | CH | NH | 1-2 | 4-Cl, 6-F | CH$_2$CO$_2$CH$_2$CH$_3$ | J1 |
| 509 | CH | NCH$_3$ | 1-2 | 4-Cl, 6-F | CH$_3$ | J1 |
| 510 | CH | NCH$_3$ | 1-2 | 4-Cl, 6-F | C$_2$H$_5$ | J1 |
| 511 | CH | NCH$_3$ | 1-2 | 4-Cl, 6-F | isopropyl | J1 |
| 512 | CH | NCH$_3$ | 1-2 | 4-Cl, 6-F | t-butyl | J1 |
| 513 | CH | NCH$_3$ | 1-2 | 4-Cl, 6-F | CF$_3$ | J1 |
| 514 | CH | NCH$_3$ | 1-2 | 4-Cl, 6-F | CF$_2$CF$_3$ | J1 |
| 515 | CH | NCH$_3$ | 1-2 | 4-Cl, 6-F | CHFCH$_3$ | J1 |
| 516 | CH | NCH$_3$ | 1-2 | 4-Cl, 6-F | CON(CH$_3$)$_2$ | J1 |
| 517 | CH | NCH$_3$ | 1-2 | 4-Cl, 6-F | CH$_2$CO$_2$C$_2$H$_5$ | J1 |
| 518 | CH | NCH$_3$ | 1-2 | 4-Cl, 6-F | CH$_2$CH$_2$CN | J1 |
| 519 | CH | NCH$_3$ | 1-2 | 4-Cl, 6-F | C(CH$_3$)$_2$OH | J1 |
| 520 | CH | NCH$_3$ | 1-2 | 4-Cl, 6-F | C(CH$_3$)$_2$OCOCH$_3$ | J1 |
| 521 | CH | NCH$_3$ | 1-2 | 4-Cl, 6-F | C(CH$_3$)$_2$NHSO$_2$CH$_3$ | J1 |
| 522 | CH | NCH$_3$ | 1-2 | 4-Cl, 6-F | CO$_2$CH$_2$CH$_3$ | J1 |

TABLE 2-continued

| | | | | | | |
|---|---|---|---|---|---|---|
| 523 | CH | NC$_2$H$_5$ | 1-2 | 4-Cl, 6-F | CH$_3$ | J1 |
| 524 | CH | NC$_2$H$_5$ | 1-2 | 4-Cl, 6-F | C$_2$H$_5$ | J1 |
| 525 | CH | NC$_2$H$_5$ | 1-2 | 4-Cl, 6-F | isopropyl | J1 |
| 526 | CH | NC$_2$H$_5$ | 1-2 | 4-Cl, 6-F | t-butyl | J1 |
| 527 | CH | NC$_2$H$_5$ | 1-2 | 4-Cl, 6-F | CF$_3$ | J1 |
| 528 | CH | NC$_2$H$_5$ | 1-2 | 4-Cl, 6-F | CO$_2$CH$_3$ | J1 |
| 529 | CH | NC$_4$H$_9$ | 1-2 | 4-Cl, 6-F | CH$_3$ | J1 |
| 530 | CH | NC$_4$H$_9$ | 1-2 | 4-Cl, 6-F | C$_2$H$_5$ | J1 |
| 531 | CH | NC$_4$H$_9$ | 1-2 | 4-Cl, 6-F | isopropyl | J1 |
| 532 | CH | NC$_4$H$_9$ | 1-2 | 4-Cl, 6-F | t-butyl | J1 |
| 533 | CH | NC$_4$H$_9$ | 1-2 | 4-Cl, 6-F | CF$_3$ | J1 |
| 534 | CH | NC$_4$H$_9$ | 1-2 | 4-Cl, 6-F | CO$_2$CH$_3$ | J1 |
| 535 | CH | NCH$_2$OCH$_3$ | 1-2 | 4-Cl, 6-F | CH$_3$ | J1 |
| 536 | CH | NCH$_2$OCH$_3$ | 1-2 | 4-Cl, 6-F | C$_2$H$_5$ | J1 |
| 537 | CH | NCO$_2$CH$_3$ | 1-2 | 4-Cl, 6-F | isopropyl | J1 |
| 538 | CH | NCH$_2$OCH$_3$ | 1-2 | 4-Cl, 6-F | t-butyl | J1 |
| 539 | CH | NCH$_2$OCH$_3$ | 1-2 | 4-Cl, 6-F | CF$_3$ | J1 |
| 540 | CH | NCH$_2$OCH$_3$ | 1-2 | 4-Cl, 6-F | CO$_2$CH$_3$ | J1 |
| 541 | CH | NCO$_2$CH$_3$ | 1-2 | 4-Cl, 6-F | CH$_3$ | J1 |
| 542 | CH | NCO$_2$CH$_3$ | 1-2 | 4-Cl, 6-F | C$_2$H$_5$ | J1 |
| 543 | CH | NCO$_2$CH$_3$ | 1-2 | 4-Cl, 6-F | isopropyl | J 1 |
| 544 | CH | NCO$_2$CH$_3$ | 1-2 | 4-Cl, 6-F | t-butyl | J1 |
| 545 | CH | NCO$_2$CH$_3$ | 1-2 | 4-Cl, 6-F | CF$_3$ | J1 |
| 546 | CH | NCO$_2$CH$_3$ | 1-2 | 4-Cl, 6-F | CO$_2$CH$_3$ | J1 |
| 547 | CH | NSO$_2$CH$_3$ | 1-2 | 4-Cl, 6-F | CH$_3$ | J1 |
| 548 | CH | NSO$_2$CH$_3$ | 1-2 | 4-Cl, 6-F | C$_2$H$_5$ | J1 |
| 549 | CH | NSO$_2$CH$_3$ | 1-2 | 4-Cl, 6-F | isopropyl | J1 |
| 550 | CH | NSO$_2$CH$_3$ | 1-2 | 4-Cl, 6-F | t-butyl | J1 |
| 551 | CH | NSO$_2$CH$_3$ | 1-2 | 4-Cl, 6-F | CF$_3$ | J1 |
| 552 | CH | NSO$_2$CH$_3$ | 1-2 | 4-Cl, 6-F | CO$_2$CH$_3$ | J1 |
| 553 | CH | NCH$_2$CHCH$_2$ | 1-2 | 4-Cl, 6-F | CH$_3$ | J1 |
| 554 | CH | NCH$_2$CHCH$_2$ | 1-2 | 4-Cl, 6-F | C$_2$H$_5$ | J1 |
| 555 | CH | NCH$_2$CHCH$_2$ | 1-2 | 4-Cl, 6-F | isopropyl | J1 |
| 556 | CH | NCH$_2$CHCH$_2$ | 1-2 | 4-Cl, 6-F | t-butyl | J1 |
| 557 | CH | NCH$_2$CHCH$_2$ | 1-2 | 4-Cl, 6-F | CF$_3$ | J1 |
| 558 | CH | NCH$_2$CHCH$_2$ | 1-2 | 4-Cl, 6-F | CO$_2$CH$_3$ | J1 |
| 559 | CH | NCH$_2$C≡CH | 1-2 | 4-Cl, 6-F | CH$_3$ | J1 |
| 560 | CH | NCH$_2$C≡CH | 1-2 | 4-Cl, 6-F | C$_2$H$_5$ | J1 |
| 561 | CH | NCH$_2$C≡CH | 1-2 | 4-Cl, 6-F | isopropyl | J1 |
| 562 | CH | NCH$_2$C≡CH | 1-2 | 4-Cl, 6-F | t-butyl | J1 |
| 563 | CH | NCH$_2$C≡CH | 1-2 | 4-Cl, 6-F | CF$_3$ | J1 |
| 564 | CH | NCH$_2$C≡CH | 1-2 | 4-Cl, 6-F | CO$_2$CH$_3$ | J1 |
| 565 | CH | NCH$_2$CO$_2$Me | 1-2 | 4-Cl, 6-F | CH$_3$ | J1 |
| 566 | CH | NCH$_2$CO$_2$Me | 1-2 | 4-Cl, 6-F | C$_2$H$_5$ | J1 |
| 567 | CH | NCH$_2$CO$_2$Me | 1-2 | 4-Cl, 6-F | isopropyl | J1 |
| 568 | CH | NCH$_2$CO$_2$Me | 1-2 | 4-Cl, 6-F | t-butyl | J1 |
| 569 | CH | NCH$_2$CO$_2$Me | 1-2 | 4-Cl, 6-F | CF$_3$ | J1 |
| 570 | CH | NCH$_2$CO$_2$Me | 1-2 | 4-Cl, 6-F | CO$_2$CH$_3$ | J1 |
| 571 | CH | NCH$_2$CHF$_2$ | 1-2 | 4-Cl, 6-F | CH$_3$ | J1 |
| 572 | CH | NCH$_2$CHF$_2$ | 1-2 | 4-Cl, 6-F | C$_2$H$_5$ | J1 |
| 573 | CH | NCH$_2$CHF$_2$ | 1-2 | 4-Cl, 6-F | isopropyl | J1 |
| 574 | CH | NCH$_2$CHF$_2$ | 1-2 | 4-Cl, 6-F | t-butyl | J1 |
| 575 | CH | NCH$_2$CHF$_2$ | 1-2 | 4-Cl, 6-F | CF$_3$ | J1 |
| 576 | CH | NCH$_2$CHF$_2$ | 1-2 | 4-Cl, 6-F | CO$_2$CH$_3$ | J1 |
| 577 | CH | NH | 1-2 | 4-Cl, 6-F | CH$_3$ | J2 |
| 578 | CH | NH | 1-2 | 4-Cl, 6-F | C$_2$H$_5$ | J2 |
| 579 | CH | NH | 1-2 | 4-Cl, 6-F | isopropyl | J2 |
| 580 | CH | NH | 1-2 | 4-Cl, 6-F | t-butyl | J2 |
| 581 | CH | NH | 1-2 | 4-Cl, 6-F | CF$_3$ | J2 |
| 582 | CH | NH | 1-2 | 4-Cl, 6-F | CO$_2$CH$_3$ | J2 |
| 583 | CH | NH | 1-2 | 4-Cl, 6-F | CH$_3$ | J3 |
| 584 | CH | NH | 1-2 | 4-Cl, 6-F | C$_2$H$_5$ | J3 |
| 585 | CH | NH | 1-2 | 4-Cl, 6-F | isopropyl | J3 |
| 586 | CH | NH | 1-2 | 4-Cl, 6-F | t-butyl | J3 |
| 587 | CH | NH | 1-2 | 4-Cl, 6-F | CF$_3$ | J3 |
| 588 | CH | NH | 1-2 | 4-Cl, 6-F | CO$_2$CH$_3$ | J3 |
| 589 | CH | NH | 1-2 | 4-Cl, 6-F | CH$_3$ | J4 |
| 590 | CH | NH | 1-2 | 4-Cl, 6-F | C$_2$H$_5$ | J4 |
| 591 | CH | NH | 1-2 | 4-Cl, 6-F | isopropyl | J4 |
| 592 | CH | NH | 1-2 | 4-Cl, 6-F | t-butyl | J4 |
| 593 | CH | NH | 1-2 | 4-Cl, 6-F | CF$_3$ | J4 |
| 594 | CH | NH | 1-2 | 4-Cl, 6-F | CO$_2$CH$_3$ | J4 |
| 595 | CH | NH | 1-2 | 4-Cl | CO$_2$CH$_2$CH$_3$ | J5 |
| 596 | CH | NH | 1-2 | 4-Cl, 6-F | CH$_3$ | J5 |
| 597 | CH | NH | 1-2 | 4-Cl, 6-F | C$_2$H$_5$ | J5 |
| 598 | CH | NH | 1-2 | 4-Cl, 6-F | isopropyl | J5 |
| 599 | CH | NH | 1-2 | 4-Cl, 6-F | t-butyl | J5 |
| 600 | CH | NH | 1-2 | 4-Cl, 6-F | CF$_3$ | J5 |
| 601 | CH | NH | 1-2 | 4-Cl, 6-F | CO$_2$CH$_3$ | J5 |

TABLE 2-continued

| | | | | | | |
|---|---|---|---|---|---|---|
| 602 | NH | CH | 2-3 | 4-Cl, 6-F | CH$_3$ | J7 |
| 603 | NH | CH | 2-3 | 4-Cl, 6-F | n-C$_3$H$_7$ | J1 |
| 604 | NH | CH | 2-3 | 4-Cl, 6-F | i-C$_3$H$_7$ | J1 |
| 605 | NH | CH | 2-3 | 4-Cl, 6-F | t-C$_4$H$_9$ | J1 |
| 606 | NH | CH | 2-3 | 4-Cl, 6-F | CH$_2$OH | J1 |
| 607 | NH | CH | 2-3 | 4-Cl, 6-F | CH$_2$CH$_2$OH | J1 |
| 608 | NH | CH | 2-3 | 4-Cl, 6-F | C(CH$_3$)$_2$OH | J1 |
| 609 | NH | CH | 2-3 | 4-Cl, 6-F | CONHCH$_3$ | J1 |
| 610 | NH | CH | 2-3 | 4-Cl, 6-F | CON(CH$_3$)$_2$ | J1 |
| 611 | NH | CH | 2-3 | 4-Cl, 6-F | CO$_2$CH$_3$ | J1 |
| 612 | NH | CH | 2-3 | 4-Cl, 6-F | Phenyl | J1 |
| 613 | NH | CH | 2-3 | 4-Cl, 6-F | CF$_2$CF$_3$ | J1 |
| 614 | NH | CH | 2-3 | 4-Cl, 6-F | CH$_2$OCH$_3$ | J1 |
| 615 | NH | CH | 2-3 | 4-Cl, 6-F | Benzyl | J1 |
| 616 | NH | CH | 2-3 | 4-Cl, 6-F | 4-chlorophenylmethyl | J1 |
| 617 | NH | CH | 2-3 | 4-Cl, 6-F | SO$_2$CH$_3$ | J1 |
| 618 | NH | CH | 2-3 | 4-Cl, 6-F | CF$_3$ | J1 |
| 619 | NH | CH | 2-3 | 4-Cl, 6-F | C(CH$_3$)$_2$OCOCH$_3$ | J1 |
| 620 | NH | CH | 2-3 | 4-Cl, 6-F | C(CH$_3$)$_2$CH$_2$OH | J1 |
| 621 | NH | CH | 2-3 | 4-Cl, 6-F | C(CH$_3$)$_2$CH$_2$OCH$_3$ | J1 |
| 622 | NH | CH | 2-3 | 4-Cl, 6-F | C$_2$H$_5$ | J1 |
| 623 | NH | CH | 2-3 | 4-Cl, 6-F | CO$_2$Na | J1 |
| 624 | NH | CH | 2-3 | 4-Cl, 6-F | CONHSO$_2$CH$_3$ | J1 |
| 625 | NH | CH | 2-3 | 4-Cl, 6-F | CHFCH$_3$ | J1 |
| 626 | NH | CH | 2-3 | 4-Cl, 6-F | CH$_2$CO$_2$CH$_2$CH$_3$ | J1 |
| 627 | NH | CH | 2-3 | 4-Cl, 6-F | CH$_3$ | J2 |
| 628 | NH | CH | 2-3 | 4-Cl, 6-F | C$_2$H$_5$ | J2 |
| 629 | NH | CH | 2-3 | 4-Cl, 6-F | isopropyl | J2 |
| 630 | NH | CH | 2-3 | 4-Cl, 6-F | t-butyl | J2 |
| 631 | NH | CH | 2-3 | 4-Cl, 6-F | CF$_3$ | J2 |
| 632 | NH | CH | 2-3 | 4-Cl, 6-F | CO$_2$CH$_3$ | J2 |
| 633 | NH | CH | 2-3 | 4-Cl, 6-F | CH$_3$ | J3 |
| 634 | NH | CH | 2-3 | 4-Cl, 6-F | C$_2$H$_5$ | J3 |
| 635 | NH | CH | 2-3 | 4-Cl, 6-F | isopropyl | J3 |
| 636 | NH | CH | 2-3 | 4-Cl, 6-F | t-butyl | J3 |
| 637 | NH | CH | 2-3 | 4-Cl, 6-F | CF$_3$ | J3 |
| 638 | NH | CH | 2-3 | 4-Cl, 6-F | CO$_2$CH$_3$ | J3 |
| 639 | NH | CH | 2-3 | 4-Cl, 6-F | CH$_3$ | J4 |
| 640 | NH | CH | 2-3 | 4-Cl, 6-F | C$_2$H$_5$ | J4 |
| 641 | NH | CH | 2-3 | 4-Cl, 6-F | isopropyl | J4 |
| 642 | NH | CH | 2-3 | 4-Cl, 6-F | t-butyl | J4 |
| 643 | NH | CH | 2-3 | 4-Cl, 6-F | CF$_3$ | J4 |
| 644 | NH | CH | 2-3 | 4-Cl, 6-F | CO$_2$CH$_3$ | J4 |
| 645 | NH | CH | 2-3 | 4-Cl, 6-F | CH$_3$ | J5 |
| 646 | NH | CH | 2-3 | 4-Cl, 6-F | C$_2$H$_5$ | J5 |
| 647 | NH | CH | 2-3 | 4-Cl, 6-F | isopropyl | J5 |
| 648 | NH | CH | 2-3 | 4-Cl, 6-F | t-butyl | J5 |
| 649 | NH | CH | 2-3 | 4-Cl, 6-F | CF$_3$ | J5 |
| 650 | NH | CH | 2-3 | 4-Cl, 6-F | CO$_2$CH$_3$ | J5 |
| 651 | NH | CCH$_3$ | 2-3 | 4-Cl, 6-F | CH$_3$ | J1 |
| 652 | NH | CCH$_3$ | 2-3 | 4-Cl, 6-F | C$_2$H$_5$ | J1 |
| 653 | NH | CCH$_3$ | 2-3 | 4-Cl, 6-F | isopropyl | J1 |
| 654 | NH | CCH$_3$ | 2-3 | 4-Cl, 6-F | t-butyl | J1 |
| 655 | NH | CCH$_3$ | 2-3 | 4-Cl, 6-F | CF$_3$ | J1 |
| 656 | NH | CCH$_3$ | 2-3 | 4-Cl, 6-F | CO$_2$CH$_3$ | J1 |
| 657 | NH | CCH$_2$CH$_3$ | 2-3 | 4-Cl, 6-F | CH$_3$ | J1 |
| 658 | NH | CCH$_2$CH$_3$ | 2-3 | 4-Cl, 6-F | C$_2$H$_5$ | J1 |
| 659 | NH | CCH$_2$CH$_3$ | 2-3 | 4-Cl, 6-F | isopropyl | J1 |
| 660 | NH | CCH$_2$CH$_3$ | 2-3 | 4-Cl, 6-F | t-butyl | J1 |
| 661 | NH | CCH$_2$CH$_3$ | 2-3 | 4-Cl, 6-F | CF$_3$ | J1 |
| 662 | NH | CCH$_2$CH$_3$ | 2-3 | 4-Cl, 6-F | CO$_2$CH$_3$ | J1 |
| 663 | NH | CCH$_2$CHF$_2$ | 2-3 | 4-Cl, 6-F | CH$_3$ | J1 |
| 664 | NH | CCH$_2$CHF$_2$ | 2-3 | 4-Cl, 6-F | C$_2$H$_5$ | J1 |
| 665 | NH | CCH$_2$CHF$_2$ | 2-3 | 4-Cl, 6-F | isopropyl | J1 |
| 666 | NH | CCH$_2$CHF$_2$ | 2-3 | 4-Cl, 6-F | t-butyl | J1 |
| 667 | NH | CCH$_2$CHF$_2$ | 2-3 | 4-Cl, 6-F | CF$_3$ | J1 |
| 668 | NH | CCH$_2$CHF$_2$ | 2-3 | 4-Cl, 6-F | CO$_2$CH$_3$ | J1 |
| 669 | NH | CH | 2-3 | 4-Cl, 6-F | CH$_3$ | J2 |
| 670 | NH | CH | 2-3 | 4-Cl, 6-F | C$_2$H$_5$ | J2 |
| 671 | NH | CH | 2-3 | 4-Cl, 6-F | isopropyl | J2 |
| 672 | NH | CH | 2-3 | 4-Cl, 6-F | t-butyl | J2 |
| 673 | NH | CH | 2-3 | 4-Cl, 6-F | CF$_3$ | J2 |
| 674 | NH | CH | 2-3 | 4-Cl, 6-F | CO$_2$CH$_3$ | J2 |
| 675 | NH | CH | 2-3 | 4-Cl, 6-F | CH$_3$ | J3 |
| 676 | NH | CH | 2-3 | 4-Cl, 6-F | C$_2$H$_5$ | J3 |
| 677 | NH | CH | 2-3 | 4-Cl, 6-F | isopropyl | J3 |
| 678 | NH | CH | 2-3 | 4-Cl, 6-F | t-butyl | J3 |
| 679 | NH | CH | 2-3 | 4-Cl, 6-F | CF$_3$ | J3 |
| 680 | NH | CH | 2-3 | 4-Cl, 6-F | CO$_2$CH$_3$ | J3 |

TABLE 2-continued

| | | | | | | |
|---|---|---|---|---|---|---|
| 681 | NH | CH | 2-3 | 4-Cl, 6-F | $CH_3$ | J4 |
| 682 | NH | CH | 2-3 | 4-Cl, 6-F | $C_2H_5$ | J4 |
| 683 | NH | CH | 2-3 | 4-Cl, 6-F | isopropyl | J4 |
| 684 | NH | CH | 2-3 | 4-Cl, 6-F | t-butyl | J4 |
| 685 | NH | CH | 2-3 | 4-Cl, 6-F | $CF_3$ | J4 |
| 686 | NH | CH | 2-3 | 4-Cl, 6-F | $CO_2CH_3$ | J4 |
| 687 | NH | CH | 2-3 | 4-Cl, 6-F | $CH_3$ | J5 |
| 688 | NH | CH | 2-3 | 4-Cl, 6-F | $C_2H_5$ | J5 |
| 689 | NH | CH | 2-3 | 4-Cl, 6-F | isopropyl | J5 |
| 690 | NH | CH | 2-3 | 4-Cl, 6-F | t-butyl | J5 |
| 691 | NH | CH | 2-3 | 4-Cl, 6-F | $CF_3$ | J5 |
| 692 | NH | CH | 2-3 | 4-Cl, 6-F | $CO_2CH_3$ | J5 |
| 693 | $NCH_3$ | CH | 2-3 | 4-Cl, 6-F | $CF_3$ | J1 |
| 694 | NH | CH | 2-3 | 4-Cl | $CF_3$ | J1 |
| 695 | CH | NH | 1-2 | 4-Cl, 6-F | $CF_3$ | J1 |
| 696 | CH | $NCH_2C_6H_5$ | 1-2 | 4-Cl, 6-F | $CF_3$ | J1 |
| 697 | CH | $NCH_2CO_2C_2H_5$ | 1-2 | 4-Cl, 6-F | $CF_3$ | J1 |
| 698 | CH | $NCOCH_3$ | 1-2 | 4-Cl, 6-F | $CF_3$ | J1 |
| 699 | CH | $NCH_2C{\equiv}N$ | 1-2 | 4-Cl, 6-F | $CF_3$ | J1 |
| 700 | CH | NH | 1-2 | 4-Cl, 6-F | $CF_3$ | J1 |
| 701 | CH | NH | 1-2 | 4-Cl, 6-F | $CO_2C_2H_5$ | J1 |
| 702 | CH | NH | 1-2 | 4-Cl | $CO_2C_2H_5$ | J1 |
| 703 | N | O | 1-2 | 4-Cl, 6-F | $CH_3$ | J7 |
| 704 | O | CH | 1-2 | 4-Cl, 6-F | $C(CH_3)_2OH$ | J7 |
| 705 | NH | N | 2-3 | 4-Cl, 6-F | $CF_3$ | J6 |
| 706 | NH | N | 2-3 | 4-Cl, 6-F | $C(CH_3)_3$ | J6 |
| 707 | NH | N | 2-3 | 4-Cl, 6-F | $CF_3$ | J7 |
| 708 | NH | N | 2-3 | 4-Cl, 6-F | $CH_2C(CH_3)_3$ | J1 |
| 709 | NH | N | 2-3 | 4-Cl, 6-F | 3,5-dimethylisoxazolyl | J1 |
| 710 | NH | N | 2-3 | 4-Cl, 6-F | pyridin-2-yl | J1 |
| 711 | $NCOCH_3$ | N | 2-3 | 4-Cl, 6-F | H | J1 |
| 712 | NH | N | 2-3 | 4-Cl, 6-F | $C_7F_{15}$ | J1 |
| 713 | NH | N | 2-3 | 4-Cl, 6-F | $CHCl_2$ | J1 |
| 714 | NH | N | 2-3 | 4-Cl, 6-F | $NHCO_2C_2H_5$ | J1 |
| 715 | NH | N | 2-3 | 4-Cl, 6-F | $CH(CH_3)NHCH_2CO_2C_2H_5$ | J1 |
| 716 | NH | N | 2-3 | 4-Cl, 6-F | $CH(CH_3)OCOCH_3$ | J1 |
| 717 | NH | N | 2-3 | 4-Cl, 6-F | $C(CH_3){=}CH_2$ | J1 |
| 718 | NH | N | 2-3 | 4-Cl, 6-F | $CH{=}C(CH_3)_2$ | J1 |
| 719 | NH | N | 2-3 | 4-Cl, 6-F | $CH(Br)CH_3$ | J1 |
| 720 | NH | N | 2-3 | 6-F | $CF_3$ | J1 |
| 721 | NH | N | 2-3 | 4-Cl, 6-F | $CH{=}NC_6H_5$ | J1 |
| 722 | NH | N | 2-3 | 4-Cl, 6-F | $CH_2OCOCH_3$ | J1 |
| 723 | NH | N | 2-3 | 4-Cl, 6-F | $CH(OCH_3)C_6H_5$ | J1 |
| 724 | NH | N | 2-3 | 4-Cl, 6-F | $CH(OCOCH_3)C_6H_5$ | J1 |
| 725 | NH | N | 2-3 | 4-Cl, 6-F | $SCH_3$ | J1 |
| 726 | NH | N | 2-3 | 4-Cl, 6-F | $C_2H_5$ | J5 |
| 727 | $NCH_3$ | N | 2-3 | $4,6\text{-}Cl_2$ | $CF_3$ | J1 |
| 728 | N | $NCH_3$ | 2-3 | $4,6\text{-}Cl_2$ | $CF_3$ | J1 |
| 729 | NH | NH | — | 4-Cl, 6-F | $CF_3$ | J1 |
| 730 | NH | N | 2-3 | $4,6\text{-}Cl_2$ | $CF_3$ | J5 |
| 731 | NH | N | 2-3 | 4-Cl, 6-F | $SO_2CH_3$ | J1 |
| 732 | NH | N | 2-3 | 4-Br, 6-F | $CF_3$ | J1 |
| 733 | NH | N | 2-3 | 4-Br, 6-F | $C_2H_5$ | J1 |
| 734 | NH | N | 2-3 | 4-Cl, 6-F | $CH_2OH$ | J1 |
| 735 | NH | N | 2-3 | 4-Cl, 6-F | $C(CH_3)_2OH$ | J1 |
| 736 | NH | N | 2-3 | 4-Cl, 6-F | $C(CH_3)OCH_2C_6H_5$ | J1 |
| 737 | NH | N | 2-3 | 4-Cl, 6-F | SH | J1 |
| 738 | NH | N | 2-3 | 4-Cl, 6-F | $SCH(CH_3)C{\equiv}N$ | J1 |
| 739 | NH | N | 2-3 | 4-Cl, 6-F | $SC_2H_5$ | J1 |
| 740 | NH | N | 2-3 | 4-Cl, 6-F | $SCH_2C{\equiv}CH$ | J1 |
| 741 | NH | N | 2-3 | 4-Cl, 6-F | $SCH_2C_6H_5$ | J1 |
| 742 | NH | N | 2-3 | 4-Cl, 6-F | $SC{\equiv}N$ | J1 |
| 743 | NH | N | 2-3 | 4-Cl, 6-F | $C(CH_3)_2CH_2SC{\equiv}N$ | J1 |
| 744 | NH | N | 2-3 | 4-Cl, 6-F | $SCH(CH_3)CO_2C_2H_5$ | J1 |
| 745 | NH | N | 2-3 | 4-Cl, 6-F | $SCH(CH_3)CON(CH_3)_2$ | J1 |
| 746 | NH | N | 2-3 | 4-Cl, 6-F | $SCH_2C{\equiv}CH$ | J5 |
| 747 | NH | N | 2-3 | 4-Cl, 6-F | $SCH_2C{=}CH_2$ | J1 |
| 748 | NH | N | 2-3 | 4-Cl, 6-F | $SCH_2C{\equiv}N$ | J1 |
| 749 | NH | N | 2-3 | 4-Cl, 6-F | $SCH_2C{\equiv}CCH_2Cl$ | J1 |
| 750 | O | CH | 2-3 | 4-Cl, 6-F | $CH_2OCONHCH_3$ | J1 |
| 751 | O | CH | 2-3 | 4-Cl, 6-F | $CH_2NHCOCH_2(C_6H_4, 2\text{-}NO_2)$ | J1 |
| 752 | O | CH | 2-3 | 4-Cl, 6-F | $C(CH_3)(OH)C_6H_5$ | J1 |
| 753 | O | CH | 2-3 | 4-Cl, 6-F | $CH_2NH_2$ | J1 |
| 754 | O | CH | 2-3 | 4-Cl, 6-F | $C(CH_3)(OH)CH(CH_3)_2$ | J1 |
| 755 | O | CH | 2-3 | 4-Cl, 6-F | $CH_2NHCOCH_3$ | J1 |
| 756 | O | CH | 2-3 | 4-Cl, 6-F | $CH_2NHSO_2CH_3$ | J1 |
| 757 | O | CH | 2-3 | 4-Cl, 6-F | $C(CH_3)_2F$ | J1 |
| 758 | O | CH | 2-3 | 4-Cl, 6-F | $CH_2CO_2H$ | J1 |

TABLE 2-continued

| | | | | | | |
|---|---|---|---|---|---|---|
| 759 | O | CH | 2-3 | 4-Cl, 6-F | $CH_2CON(CH_3)_2$ | J1 |
| 760 | O | CH | 2-3 | 4-Cl, 6-F | $CH_2CON(CH_3)(OCH_3)$ | J1 |
| 761 | O | CH | 2-3 | 4-Cl, 6-F | $CH_2CONHCH_3$ | J1 |
| 762 | O | CH | 2-3 | 4-Cl, 6-F | $CH_2CONH_2$ | J1 |
| 763 | O | CH | 2-3 | 4-Cl, 6-F | $C_2H_4CON(CH_3)(OCH_3)$ | J1 |
| 764 | O | CH | 2-3 | 4-Cl, 6-F | $C_2H_4CO_2CH_3$ | J1 |
| 765 | O | CH | 2-3 | 4-Cl, 6-F | $C_3H_6OH$ | J1 |
| 766 | O | CH | 2-3 | 4-Cl, 6-F | $C_2H_4CONHCH_3$ | J1 |
| 767 | NH | N | 2-3 | 4-Cl | $SCF_3$ | J1 |
| 768 | NH | N | 2-3 | 4-Cl | $CF_3$ | J1 |
| 769 | NH | N | 2-3 | 4-Cl | $CF_3$ | J3 |

TABLE 3

Characterizing Data
Melting Points or Physical States of Representative Compounds

| No. | MP/State | No. | MP/State | No. | MP/State | No. | MP/State |
|---|---|---|---|---|---|---|---|
| 1 | OIL | 246 | 45–9 | 377 | 122–30 | 722 | 117–122 RESIN |
| 16 | 70–72 | 247 | 35–8 | 378 | 200 C> | 723 | 107–112 RESIN |
| 25 | OIL | 248 | 67–71 | 379 | 116–22 | 724 | 108–114 RESIN |
| 26 | OIL | 249 | 84–9 | 380 | 201–4 | 725 | 135–140 RESIN |
| 28 | OIL | 250 | 65–68 | 381 | 117–24 | 726 | >210 |
| 30 | OIL | 251 | 55–7 | 382 | 193–5 | 727 | 182–183 |
| 38 | 246–9 | 252 | OIL | 383 | 131–40 | 728 | 174–175 |
| 42 | >250 | 253 | GLASS | 384 | 103–5 | 729 | >205 |
| 43 | SOLID | 254 | 71–5 | 385 | 158–160 | 730 | >205 |
| 49 | OIL | 255 | 134–8 | 386 | 132–5 | 731 | 150–152 RESIN |
| 96 | OIL | 256 | 145–7 | 387 | 112–4 | 732 | 195–200 |
| 98 | >245 | 257 | OIL | 388 | 107–9 | 733 | >205 |
| 99 | OIL | 258 | 232–40 | 399 | 177.5–8.5 | 734 | SOLID |
| 100 | OIL | 259 | 165–9 | 405 | 130 | 735 | 118–121 RESIN |
| 101 | OIL | 260 | 55–8 | 469 | 98–100 | 736 | 88–92 |
| 102 | OIL | 261 | 65–7 | 481 | SOLID | 737 | >200 |
| 103 | OIL | 262 | 75–7 | 493 | 187–8 | 738 | 133–135 |
| 104 | OIL | 263 | >50 | 500 | 208–10 | 739 | 130–132 |
| 105 | >250 | 264 | 155–7 | 513 | 178–181 | 740 | 178–180 |
| 106 | OIL | 265 | 130–6 | 522 | 78–80 | 741 | 118–121 RESIN |
| 107 | OIL | 266 | 258–61 | 527 | 152–154 | 742 | 150–155 |
| 108 | >250 | 267 | 110–8 | 563 | 165–166 | 743 | SOLID |
| 109 | OIL | 268 | 73–7 | 595 | >240 | 744 | 160–162 |
| 110 | OIL | 269 | 270–5 | 618 | 235–237.5 | 745 | >200 |
| 112 | 86–88 | 270 | 265–72 | 693 | 60–65 | 746 | 106–109 |
| 221 | 193.5–6 | 271 | 62–72 | 694 | 221.5–223 | 747 | 98–100 |
| 222 | 183–6 | 272 | OIL | 695 | 160–162 | 748 | 104–110 RESIN |
| 223 | OIL | 273 | 220–2.5 | 696 | 173–177 | 749 | 155–158 RESIN |
| 224 | OIL | 274 | 116 SOFTENS | 697 | 60–63 | 750 | 137–139 |
| 225 | OIL | 275 | OIL | 698 | 142–145.5 | 751 | 189–190 |
| 226 | 63–6 | 276 | 145–53 | 699 | 95–102 | 752 | 78–82 |
| 227 | 134–6 | 277 | 179–82 | 700 | 160–162 | 753 | 87–89 |
| 228 | 42–5 | 278 | 189–92 | 701 | 245–248 | 754 | 75–77 |
| 229 | OIL | 279 | 197–8 | 702 | 258–260 | 755 | 96–98 |
| 230 | 163–5 | 280 | 215–6 | 705 | 102–103 | 756 | 90–92 |
| 231 | 65–70 | 362 | 152–8 | 706 | 88–89 | 757 | 60–62 |
| 232 | 186–91 | 363 | >165 | 708 | 140 DEC | 758 | 95–97 |
| 233 | 85–90 | 364 | SOLID | 709 | >200 | 759 | 144–146 |
| 234 | 65–70 | 365 | 172–7 | 710 | 130 RESIN | 760 | 146–147 |
| 235 | 63–7 | 366 | 130 | 711 | >200 | 761 | 70–76 |
| 236 | 56–8 | 367 | 150–5 | 712 | 93–98 RESIN | 762 | 185–187 |
| 237 | 141–2 | 368 | 87–93 | 713 | 123–130 RESIN | 763 | 63–65 |
| 238 | 143–5 | 369 | 125–30 | 714 | 160–165 RESIN | 754 | OIL |
| 239 | 162–4 | 370 | 130 | 715 | 90–95 | 765 | 50–54 |
| 240 | 72–6 | 371 | SOLID | 716 | 115–120 RESIN | 766 | 172–173 |
| 241 | 67–70 | 372 | SOLID | 717 | 120–125 | 767 | 239–241 |
| 242 | 163–5 | 373 | 160 | 718 | 110–116 | | |
| 243 | 51–55 | 374 | 190 | 719 | 120–125 | | |
| 244 | OIL | 375 | >200 | 720 | 128–132 RESIN | | |
| 245 | OIL | 376 | 142–8 | 721 | 145–150 | | |

Biological Testing

The benzofused heterocyclic compounds of this invention were tested for pre- and postemergence herbicidal activity using a variety of crops and weeds. The test plants included soybean (*Glycine max* var. Winchester), field corn (*Zea mays* var. Pioneer 3732), wheat (*Triticum aestivum* var. Lew), morningglory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 9–14 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total, Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 12–17 days the plants were examined and the phytotoxicity data were recorded.

Herbicidal activity data at selected application rates are given for various compounds of this invention in Table 4 and Table 5. The test compounds are identified by numbers which correspond to those in Tables 1 and 2.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

Herbicide Rating System

| Rating Percent Control | Description of Main Categories | Crop Description | Weed Description |
|---|---|---|---|
| 0 | No effect | No crop reduction/injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss satisfactory | Control somewhat less than satisfactory |
| 80 | Severe | Crop nearly destroyed a few survivors | Satisfactory to weed control |
| 90 | | Only occasional live plants left | Very good to excellent control |
| 100 | Complete effect | Complete crop destruction | Complete weed destruction |

Formulation

The compounds of the present invention were tested in the laboratory as water/acetone (50/50) solutions containing 0.5% v/v sorbitan monolaurate emulsifier. It is expected that all formulations normally employed in applications of herbicides would be usable with the compounds of the present invention. These include wettable powders, emulsifiable concentrates, water suspensions, flowable concentrates, and the like.

TABLE 4

PREEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 1 | 100 | 85 | 90 | 100 | 100 | 100 | 100 | 90 | 100 | 95 |
| 16 | 100 | 70 | 90 | 100 | 100 | 100 | 90 | 80 | 100 | 95 |
| 25 | 100 | 100 | 100 | 100 | 100 | 100 | 95 | 90 | 100 | 100 |

TABLE 4-continued

PREEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 26 | 100 | 90 | 90 | 100 | 100 | 100 | 100 | 95 | 100 | 100 |
| 28 | 100 | 100 | 95 | 100 | 100 | 100 | 100 | 100 | 100 | 100 |
| 30 | 100 | 100 | 95 | 100 | 100 | 100 | 90 | 100 | 100 | 100 |
| 38 | 60 | 50 | 80 | 100 | 100 | 0 | 70 | 30 | 75 | 60 |
| 42 | 0 | 10 | 0 | 100 | 60 | 30 | 20 | 50 | 30 | 0 |
| 43 | 50 | 40 | 80 | 100 | 100 | 10 | — | 60 | 70 | 80 |
| 49 | 95 | 50 | 80 | 100 | 100 | 20 | 90 | — | 100 | 90 |
| 96 | 100 | 90 | 95 | 100 | 100 | 100 | — | 90 | 100 | 95 |
| 98 | 50 | 40 | 80 | 80 | 75 | 70 | 60 | 10 | 30 | 65 |
| 99 | 40 | 50 | 60 | 100 | 100 | 100 | — | 60 | 100 | 65 |
| 100 | 40 | 30 | 80 | 100 | 100 | 20 | — | 60 | 50 | 70 |
| 101 | 80 | 70 | 100 | 100 | 100 | — | 80 | 80 | 100 | 100 |
| 102 | 20 | 30 | 10 | 100 | 70 | — | 50 | 90 | 100 | 60 |
| 103 | 50 | 50 | 80 | 100 | 100 | — | 70 | 90 | 100 | 70 |
| 104 | 100 | 100 | 100 | 100 | 100 | — | 100 | 100 | 100 | 100 |
| 106 | 30 | 40 | 70 | 100 | 100 | 95 | 60 | 70 | 90 | [001b]55 |
| 107 | 80 | 60 | 90 | 100 | 100 | 100 | 40 | 75 | 100 | 100 |
| 108 | 0 | 0 | 10 | 70 | 50 | 40 | 10 | 50 | 50 | 30 |
| 109 | 100 | 100 | 90 | 100 | 100 | 100 | 100 | 100 | 100 | 100 |
| 110 | 100 | 50 | 70 | 100 | 90 | 100 | 40 | 80 | 100 | 100 |
| 112 | 100 | 100 | 100 | 100 | 100 | 100 | 100 | 100 | 100 | 100 |
| 221 | 70 | 60 | 85 | 100 | 100 | 80 | ND | ND | 100 | 95 |
| 222 | 100 | 70 | 90 | 100 | 100 | 100 | 100 | ND | 100 | 100 |
| 223 | 100 | 50 | 80 | 100 | 100 | 100 | 90 | ND | 100 | 100 |
| 224 | 100 | 80 | 90 | 100 | 100 | 100 | 95 | 80 | 100 | 100 |
| 225 | 40 | 20 | 30 | 90 | 50 | 70 | 50 | ND | 100 | 60 |
| 226 | 70 | 50 | 70 | 100 | 90 | 90 | 60 | ND | 100 | 80 |
| 227 | 100 | 80 | 90 | 100 | 100 | 100 | ND | 95 | 100 | 100 |
| 228 | 100 | 80 | 95 | 100 | 100 | 100 | 90 | ND | 100 | 100 |
| 229 | 100 | 70 | 90 | 100 | 100 | 100 | 95 | 80 | 100 | 100 |
| 230 | 100 | 40 | 80 | 100 | 100 | 100 | 100 | 80 | 100 | 100 |
| 231 | 100 | 80 | 100 | 100 | 100 | 100 | 100 | 90 | 100 | 100 |
| 232 | 20 | 30 | 50 | 90 | 80 | 20 | 10 | ND | 40 | 25 |
| 233 | 40 | 30 | 70 | 100 | 95 | 20 | 20 | ND | 60 | 50 |
| 234 | 100 | 100 | 100 | 100 | 100 | 100 | 100 | 80 | 100 | 100 |
| 235 | 100 | 90 | 100 | 100 | 100 | 100 | 100 | 80 | 100 | 100 |
| 236 | 100 | 70 | 95 | 100 | 100 | 100 | 100 | 80 | 100 | 100 |
| 237 | 100 | 90 | 90 | 100 | 100 | 100 | 100 | 100 | 100 | 100 |
| 238 | 100 | 60 | 70 | 100 | 100 | 60 | 80 | 50 | 90 | 90 |
| 239 | 100 | 70 | 90 | 100 | 100 | 100 | ND | ND | 100 | 90 |
| 240 | 100 | 95 | 95 | 100 | 100 | 100 | 100 | ND | 100 | 100 |
| 241 | 60 | 70 | 95 | 100 | 100 | 100 | 100 | ND | 100 | 100 |
| 242 | 100 | 100 | 100 | 100 | 100 | 100 | 100 | 100 | 100 | 100 |
| 243 | 100 | 80 | 95 | 100 | 100 | 100 | 100 | ND | 100 | 100 |
| 244 | 95 | 80 | 100 | 100 | 90 | 70 | 100 | 70 | 100 | 100 |
| 245 | 100 | 60 | 80 | 100 | 100 | 90 | 100 | 70 | 100 | 80 |
| 246 | 100 | 100 | 100 | 100 | 100 | 100 | 100 | 100 | 100 | 100 |
| 247 | 100 | 90 | 90 | 100 | 100 | 95 | 100 | 85 | 100 | 100 |
| 248 | 100 | 90 | 95 | 100 | 100 | 100 | 100 | 95 | 100 | 100 |
| 249 | 100 | 80 | 95 | 100 | 100 | 100 | 90 | 80 | 10 | 100 |
| 250 | 80 | 40 | 50 | 100 | 100 | ND | 100 | 60 | 100 | 70 |
| 251 | 90 | 90 | 95 | 100 | 100 | 95 | 100 | 90 | 100 | 100 |
| 252 | 100 | 100 | 100 | 100 | 100 | 100 | ND | 100 | 100 | 100 |
| 253 | 100 | 95 | 100 | 100 | 100 | 100 | ND | ND | 100 | 100 |
| 254 | 25 | 20 | 80 | 100 | 50 | 30 | 50 | 60 | 100 | 80 |
| 255 | 100 | 90 | 95 | 100 | 100 | 100 | 100 | ND | 100 | 100 |
| 256 | 100 | 80 | 95 | 100 | 100 | 100 | ND | 70 | 100 | 90 |
| 257 | 40 | 0 | 10 | 90 | 70 | 0 | 20 | 20 | 70 | 10 |
| 258 | 30 | 30 | 75 | 100 | 60 | 0 | 60 | ND | 40 | 40 |
| 259 | 70 | 40 | 80 | 100 | 70 | 100 | 55 | ND | 100 | 95 |
| 260 | 100 | 70 | 80 | 100 | 100 | 100 | 100 | 95 | 100 | 100 |
| 261 | 100 | 80 | 95 | 100 | 100 | 100 | 90 | 80 | 100 | 100 |
| 262 | 90 | 40 | 40 | 100 | 100 | 100 | 100 | 50 | 100 | 70 |
| 263 | 100 | 50 | 65 | 100 | 100 | 100 | 95 | 75 | 100 | 70 |
| 264 | 0 | 0 | 10 | 20 | 0 | 20 | 30 | 0 | 10 | 10 |
| 265 | 70 | 40 | 80 | 90 | 100 | 20 | 70 | ND | 80 | 60 |
| 266 | 50 | 30 | 60 | 40 | 70 | 0 | 0 | ND | 30 | 30 |
| 267 | 0 | 10 | 20 | 10 | 10 | 0 | 50 | 50 | 5 | 0 |
| 268 | 30 | 30 | 50 | 100 | 95 | 20 | 0 | ND | 60 | 60 |
| 269 | 60 | 30 | 80 | 100 | 100 | 100 | 100 | 70 | 100 | 75 |
| 270 | 70 | 70 | 90 | 100 | 100 | ND | 60 | 65 | 100 | 100 |
| 271 | 80 | 70 | 90 | 100 | 100 | 100 | 100 | 80 | 100 | 90 |
| 272 | 20 | 0 | 20 | 100 | 70 | 100 | 20 | 70 | 90 | 60 |
| 273 | 100 | 80 | 90 | 100 | 100 | 100 | 100 | 90 | 100 | 100 |
| 274 | 100 | 100 | 90 | 100 | 100 | 90 | 100 | 95 | 100 | 100 |

TABLE 4-continued

PREEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 275 | 100 | 80 | 100 | 100 | 100 | 100 | 100 | 80 | 100 | 95 |
| 362 | 100 | 100 | 100 | 100 | 100 | 100 | 100 | 100 | 100 | 100 |
| 363 | 100 | 100 | 100 | 100 | 100 | 100 | 100 | 100 | 100 | 100 |
| 364 | 100 | 60 | 80 | 100 | 100 | 100 | 100 | 80 | 100 | 80 |
| 365 | ND | 30 | 30 | 100 | 100 | 100 | 100 | 60 | 75 | 60 |
| 366 | 10 | 10 | 0 | 70 | 20 | 0 | 10 | 0 | 50 | 40 |
| 367 | 100 | 95 | 100 | 100 | 100 | 100 | 100 | 90 | 100 | 100 |
| 368 | 100 | 100 | 95 | 100 | 100 | 100 | 100 | 95 | 100 | 100 |
| 369 | 100 | 100 | 100 | 100 | 100 | 100 | 100 | 100 | 100 | 100 |
| 370 | 100 | 100 | 95 | 100 | 100 | 100 | 100 | 90 | 100 | 100 |
| 371 | 100 | 95 | 100 | 100 | 100 | 100 | 100 | 100 | 100 | 100 |
| 372 | 100 | 90 | 95 | 100 | 100 | 100 | 100 | 80 | 100 | 80 |
| 373 | 100 | 70 | 90 | 100 | 100 | 100 | 100 | 70 | 100 | 90 |
| 374 | 30 | 0 | 10 | 100 | 95 | 90 | 80 | 40 | 100 | 75 |
| 375 | 80 | 30 | 90 | 100 | 80 | 95 | 80 | 80 | 100 | 95 |
| 376 | 50 | 60 | 80 | 100 | 100 | 100 | 100 | 100 | 100 | 70 |
| 377 | 100 | 70 | 90 | 100 | 100 | ND | 100 | 100 | 100 | 100 |
| 378 | 90 | 70 | 90 | 100 | 100 | 100 | 100 | 80 | 100 | 95 |
| 379 | 100 | 50 | 70 | 100 | 100 | ND | 100 | 80 | 100 | 95 |
| 380 | 80 | 35 | 20 | 100 | 100 | ND | 80 | 90 | 100 | 70 |
| 381 | 100 | 40 | 80 | 100 | 100 | ND | 100 | 90 | 100 | 80 |
| 382 | 60 | 45 | 30 | 100 | 70 | ND | 60 | 90 | 95 | 80 |
| 383 | 80 | 40 | 20 | 100 | 60 | ND | 70 | 80 | 75 | 55 |
| 399 | 95 | 80 | 95 | 100 | 95 | 100 | 70 | 60 | 100 | 0 |
| 493 | 80 | 70 | 90 | 100 | 100 | 100 | 70 | 75 | 100 | 100 |
| 500 | 95 | 75 | 90 | 100 | 100 | 100 | 100 | 75 | 100 | 100 |
| 522 | 90 | 40 | 80 | 100 | 100 | 100 | 50 | 75 | 100 | 100 |
| 595 | 10 | 0 | 0 | 60 | 50 | 10 | 20 | ND | 0 | 40 |

Rate of Application is 0.3 Kg/Ha. SOY is soybean; WHT is wheat; CRN is corn; ABUTH is velvetleaf; IPOSS is morningglory; STEME is chickweed; XANPE is cocklebur; ALOMY is blackgrass, SETVI is green foxtail; SORHA is johnsongrass

TABLE 5

POSTEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 1 | 95 | 65 | 80 | 100 | 100 | 90 | 100 | 70 | 80 | 80 |
| 16 | 95 | 60 | 80 | 100 | 100 | 70 | 95 | 70 | 80 | 80 |
| 25 | 100 | 80 | 90 | 100 | 100 | 100 | 100 | 80 | 100 | 90 |
| 26 | 96 | 60 | 80 | 100 | 100 | 80 | 100 | 80 | 100 | 80 |
| 28 | 100 | 80 | 80 | 100 | 100 | 100 | 90 | 100 | 100 | 95 |
| 30 | 95 | 80 | 90 | 100 | 100 | 100 | 100 | 90 | 100 | 100 |
| 38 | 70 | 35 | 60 | 100 | 100 | 0 | 45 | 20 | 40 | 50 |
| 42 | 65 | 30 | 60 | 90 | 60 | — | 50 | 40 | 100 | 20 |
| 43 | 80 | 30 | 70 | 100 | 100 | 70 | 50 | — | 50 | 50 |
| 49 | 95 | 70 | 80 | 100 | 100 | 40 | 30 | — | 100 | 90 |
| 96 | 100 | 90 | 90 | 100 | 100 | 100 | 100 | — | 100 | 100 |
| 98 | 40 | 10 | 50 | 60 | 20 | 5 | 20 | 5 | 40 | 20 |
| 99 | 80 | 40 | 80 | 100 | 100 | 95 | 70 | — | 70 | 65 |
| 100 | 85 | 40 | 60 | 90 | 100 | 50 | 50 | — | 30 | 40 |
| 101 | 95 | 50 | 80 | 100 | 100 | — | — | 60 | 65 | 65 |
| 102 | 80 | 30 | 75 | 100 | 100 | — | — | 60 | 90 | 60 |
| 103 | 90 | 50 | 80 | 100 | 80 | — | 80 | 70 | 100 | 60 |
| 104 | 100 | 100 | 100 | 100 | 100 | — | — | — | 100 | 100 |
| 106 | 80 | 30 | 75 | 100 | 100 | — | — | 60 | 100 | 70 |
| 107 | 95 | 40 | 100 | 100 | 100 | 100 | — | 90 | 100 | 100 |
| 108 | 50 | 20 | 60 | 20 | 60 | 0 | 10 | 10 | 70 | 20 |
| 109 | 90 | 90 | 80 | 100 | 100 | — | 100 | 90 | 100 | 90 |
| 110 | 80 | 40 | 50 | 100 | 100 | 100 | 70 | 80 | 70 | |
| 112 | 100 | 100 | 100 | 100 | 100 | 100 | 100 | 100 | 100 | 100 |
| 221 | 95 | 50 | 60 | 100 | 100 | 100 | 60 | 40 | 70 | 70 |
| 222 | 100 | 70 | 90 | 100 | 100 | 100 | 100 | 100 | 100 | 100 |
| 223 | 95 | 40 | 90 | 100 | 100 | 100 | 100 | ND | 100 | 100 |
| 224 | 95 | 70 | 100 | 100 | 100 | 100 | 100 | 90 | 100 | ND |
| 225 | 60 | 30 | 60 | 100 | 75 | ND | 70 | ND | 90 | 60 |
| 226 | 70 | 40 | 80 | 100 | 95 | 80 | 90 | ND | 100 | 80 |
| 227 | 95 | 60 | 90 | 100 | 100 | 100 | 100 | 100 | 100 | 100 |
| 228 | 90 | 50 | 80 | 100 | 100 | 80 | 95 | ND | 100 | 90 |
| 229 | 95 | 60 | 80 | 100 | 100 | 100 | 100 | 70 | 100 | 100 |
| 230 | 95 | 40 | 80 | 100 | 100 | 90 | 100 | 70 | 100 | 90 |

TABLE 5-continued

POSTEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 231 | 100 | 70 | 100 | 100 | 100 | 100 | ND | 100 | 100 | 100 |
| 232 | 75 | 50 | 30 | 100 | 80 | 20 | 40 | ND | 30 | 10 |
| 233 | 90 | 30 | 60 | 100 | 100 | 30 | 30 | ND | 30 | 30 |
| 234 | 100 | 100 | 100 | 100 | 100 | 100 | 100 | 100 | 100 | 100 |
| 235 | 100 | 100 | 100 | 100 | 100 | 100 | 100 | 100 | 100 | 100 |
| 236 | 100 | 75 | 90 | 100 | 100 | 100 | 100 | 80 | 100 | 100 |
| 237 | 100 | 95 | 100 | 100 | 100 | ND | 100 | 100 | 100 | 100 |
| 238 | 80 | 30 | 70 | 100 | 100 | ND | 100 | 40 | 80 | 70 |
| 239 | 95 | 60 | 80 | 100 | 100 | 100 | 100 | ND | 100 | 80 |
| 240 | 95 | 95 | 100 | 100 | 100 | 100 | 100 | ND | 100 | 100 |
| 241 | 90 | 60 | 70 | 100 | 100 | 85 | 95 | ND | 100 | 70 |
| 242 | 100 | 100 | 100 | 100 | 100 | 100 | 100 | 100 | 100 | 100 |
| 243 | 95 | 70 | 95 | 100 | 100 | 100 | 100 | ND | 100 | 100 |
| 244 | 95 | 60 | 90 | 100 | 100 | 100 | 100 | 75 | 100 | ND |
| 245 | 85 | 40 | 75 | 100 | 100 | 60 | 70 | 50 | 70 | 70 |
| 246 | 95 | 100 | 100 | 100 | 100 | 100 | 100 | ND | 100 | 100 |
| 247 | 95 | 80 | 100 | 100 | 100 | 100 | 100 | 100 | 100 | ND |
| 248 | 80 | 50 | 95 | 100 | 100 | 100 | 100 | ND | 100 | 100 |
| 249 | 95 | 80 | 100 | 100 | 100 | 100 | 100 | 100 | 100 | ND |
| 250 | 95 | 50 | 80 | 100 | 100 | 80 | 100 | 40 | 100 | 100 |
| 251 | 95 | 70 | 90 | 100 | 100 | 100 | 95 | 100 | 100 | 95 |
| 252 | 95 | 90 | 100 | 100 | 100 | 100 | ND | 100 | 100 | 100 |
| 253 | 95 | 100 | 100 | 100 | 100 | 100 | 100 | ND | 100 | 100 |
| 254 | 95 | 40 | 80 | 100 | 70 | ND | 95 | 50 | 100 | 80 |
| 255 | 100 | 100 | 100 | 100 | 100 | 100 | 100 | ND | 100 | 100 |
| 256 | 100 | 80 | 90 | 100 | 100 | 100 | 100 | 80 | 100 | 100 |
| 257 | 70 | 20 | 70 | 100 | 60 | 30 | 70 | 30 | 70 | 50 |
| 258 | 80 | 30 | 60 | 80 | 70 | 5 | 50 | 30 | 60 | 50 |
| 259 | 80 | 35 | 75 | 100 | 90 | 30 | 70 | 55 | 80 | 70 |
| 260 | 90 | 80 | 70 | 100 | 100 | ND | 100 | 90 | 100 | 90 |
| 261 | 95 | 80 | 100 | 100 | 100 | 100 | 100 | 100 | 100 | 100 |
| 262 | 95 | 60 | 80 | 100 | 100 | 95 | 95 | 50 | 100 | 80 |
| 263 | 95 | 80 | 90 | 100 | 100 | 100 | 100 | 60 | 90 | 70 |
| 264 | 50 | 20 | 50 | 40 | 40 | 0 | 30 | 0 | ND | 20 |
| 265 | 70 | 40 | 60 | 100 | 100 | 30 | 20 | ND | 40 | 20 |
| 266 | 60 | 40 | 60 | 50 | 60 | 10 | 10 | ND | 40 | 40 |
| 267 | 50 | 15 | 50 | 80 | 40 | 10 | 10 | 20 | 30 | 20 |
| 268 | 70 | 40 | 60 | 50 | 90 | 20 | ND | ND | 70 | 40 |
| 269 | 90 | 40 | 70 | 100 | 80 | 80 | ND | ND | 70 | 60 |
| 270 | 70 | 40 | 50 | 100 | 60 | 40 | ND | 50 | 50 | 50 |
| 271 | 80 | 40 | 60 | 100 | 100 | 100 | ND | ND | 70 | 50 |
| 272 | 50 | 30 | 45 | 100 | 60 | 50 | 50 | 20 | 70 | 40 |
| 273 | 95 | 60 | 95 | 100 | 100 | 90 | 100 | 80 | 100 | 100 |
| 274 | 95 | 60 | 95 | 100 | 100 | 90 | 100 | 90 | 100 | 100 |
| 275 | 100 | 70 | 90 | 100 | 100 | 100 | 100 | 95 | 100 | 100 |
| 362 | 100 | 100 | 100 | 100 | 100 | 100 | ND | 100 | 100 | 100 |
| 363 | 100 | 100 | 100 | 100 | 100 | ND | 100 | 100 | 100 | 100 |
| 364 | 95 | 40 | 80 | 100 | 100 | 100 | 100 | ND | 100 | 100 |
| 365 | 100 | 40 | 70 | 100 | 100 | 100 | ND | 70 | 80 | 30 |
| 366 | 70 | 30 | 80 | 95 | 80 | 30 | 100 | 30 | 50 | 50 |
| 367 | 100 | 100 | 100 | 100 | 100 | 100 | 100 | 100 | 100 | 100 |
| 368 | 100 | 100 | 100 | 100 | 100 | 100 | 100 | 100 | 100 | 100 |
| 369 | 100 | 80 | 100 | 100 | 100 | ND | 100 | 100 | 100 | 100 |
| 370 | 100 | 95 | 100 | 100 | 100 | 100 | 100 | 100 | 100 | 100 |
| 371 | 95 | 100 | 100 | 100 | 100 | 100 | 100 | ND | 100 | 100 |
| 372 | 100 | 100 | 100 | 100 | 100 | 100 | 100 | 100 | 100 | 100 |
| 373 | 100 | 80 | 100 | 100 | 100 | 100 | 100 | 100 | 100 | 100 |
| 374 | 80 | 25 | 30 | 100 | 95 | 80 | 100 | 25 | 80 | 60 |
| 375 | 95 | 40 | 90 | 100 | 95 | 100 | 100 | 90 | 80 | 100 |
| 376 | 90 | 50 | 95 | 100 | 100 | ND | 100 | 90 | 100 | 100 |
| 377 | 95 | 80 | 100 | 100 | 100 | ND | 100 | 100 | 100 | 100 |
| 378 | 90 | 40 | 90 | 100 | 90 | ND | 100 | 80 | 100 | 100 |
| 379 | 95 | 80 | 100 | 100 | 100 | ND | 100 | 70 | 100 | 100 |
| 380 | 95 | 30 | 95 | 100 | 100 | ND | 100 | 70 | 100 | 80 |
| 381 | 95 | 40 | 95 | 100 | 100 | ND | 100 | 100 | 100 | 100 |
| 382 | 80 | 40 | 100 | 100 | 100 | ND | 100 | 80 | 90 | 80 |
| 383 | 95 | 40 | 95 | 100 | 95 | ND | 100 | 60 | 95 | 70 |
| 399 | 95 | 30 | 70 | 100 | 100 | 100 | 100 | 50 | 70 | 60 |
| 493 | 95 | 60 | 90 | 100 | 100 | 80 | 100 | 65 | 100 | 100 |
| 500 | 95 | 65 | 95 | 100 | 100 | 90 | 100 | 80 | 100 | 100 |

TABLE 5-continued

POSTEMERGENCE HERBICIDAL ACTIVITY (% CONTROL)

| No. | SOY | WHT | CRN | ABUTH | IPOSS | STEME | XANPE | ALOMY | SETVI | SORHA |
|---|---|---|---|---|---|---|---|---|---|---|
| 522 | 90 | 45 | 90 | 100 | 100 | 100 | 100 | 50 | 100 | 100 |
| 595 | 50 | 10 | 60 | 30 | 40 | 0 | 20 | 10 | 20 | 20 |

Rate of Application is 0.3 Kg/Ha. SOY is soybean; WHT is wheat; CRN is corn; ABUTH is velvetleaf; IPOSS is morningglory; STEME is chickweed; XANPE is cocklebur; ALOMY is blackgrass, SETVI is green foxtail; SORHA is johnsongrass Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word -about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for post-emergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of the present invention may also be used in combination with other herbicides. Such herbicides include, for example: N-(phosphonomethyl) glycine (—glyphosate"); aryloxyalkanoic acids such as (2,4-dichlorophenoxy)acetic acid (-2,4-D"), (4-chloro-2-methylphenoxy)acetic acid (—MCPA"), (+/−)-2-(4-chloro-2-methylphenoxy)propanoic acid (MCPP); ureas such as N,N-dimethyl-N'-[4-(1-methylethyl)phenyl]urea (-isoproturon"); imidazolinones such as 2-[4,5-dihydro-4-methyl-4-(1-methylethyl)-5-oxo-1H-imidazol-2-yl]-3-pyridinecarboxylic acid (-imazapyr"), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid (-imazamethabenz"), (+/−)-2-[4,5-dihydro-4-methyl-4-(1-methylethyl)-5-oxo-1H-imidazol-2-yl]-5-ethyl-3-pyridinecarboxylic acid (-imazethapyr"), and (+/−)-2-[4,5-dihydro-4-methyl-4-(1-methylethyl)-5-oxo-1H-imidazol-2-yl]-3-quinolinecarboxylic acid (-imazaquin"); diphenyl ethers such as 5-[2-chloro-4-(trifluoromethyl)phenoxy]-2-nitrobenzoic acid (-acifluorfen"), methyl 5-(2,4-dichlorophenoxy)-2-nitrobenzoate (-bifenox"), and 5-[2-chloro-4-(trifluoromethyl)phenoxy]-N-(methylsulfonyl)-2-nitrobenzamide (-fomasafen"); hydroxy-benzonitriles such as 4-hydroxy-3,5-diiodobenzonitrile (-ioxynil") and 3,5-dibromo-4-hydroxybenzonitrile (-bromoxynil"); sulfonylureas such as 2-[[[[(4-chloro-6-methoxy-2-pyrimidinyl)amino]carbonyl]amino]sulfonyl]benzoic acid (-chlorimuron"), 2-chloro-N-[[(4-methoxy-6-methyl-1,3,5-triazin-2-yl)amino]carbonyl]benzenesulfonamide (-chlorsulfuron") , 2-[[[[[(4,6- dimethoxy-2-pyrimidinyl)amino]carbonyl]amino]sulfonyl]methyl]benzoic acid (-bensulfuron"), 2-[[[[(4,6-dimethoxy-2-pyrimidinyl)amino]carbonyl]amino]sulfonyl]-1-methyl-1H-pyrazol-4-carboxylic acid (-pyrazosulfuron"), 3-[[[[(4-methoxy-6-methyl-1,3,5-triazin-2-yl)amino]carbonyl]amino]sulfonyl]-2-thiophenecarboxylic acid (-thifensulfuron"), and 2-(2-chloroethoxy)-N-[[(4-methoxy-6-methyl-1,3,5-triazin-2-yl)amino]carbonyl]benzenesulfonamide (-triasulfuron"); 2-(4-aryloxyphenoxy)alkanoic acids such as (+/−)-2-[4-[(6-chloro-2-benzoxazolyl)oxy]phenoxy]propanoic acid (-fenoxaprop"), (+/−)-2-[4-[[5-(trifluoromethyl)-2-pyridinyl]oxy]phenoxy]propanoic acid (-fluazifop"), (+/−)-2-[4-(6-chloro-2-quinoxalinyl)oxy]phenoxy]propanoic acid (-quizalofop"), and (+/−)-2-[-(2,4-dichlorophenoxy)phenoxy]propanoic acid (-diclofop"); benzothiadiazinones such as 3-(1-methylethyl)-1H-2,1,3-benzothiadiazin-4(3H)-one 2,2-dioxide (-bentazone"); 2-chloroacetanilides such as N-butoxymethyl)-2-chloro-2', 6'-diethylacetanilide (-butachlor"); 2-chloro-N-(2-ethyl-6-methylphenyl)-N-(2-methoxy-1-methylethyl)acetamide (-metachlor"), 2-chloro-N-(ethoxymethyl)-N-(2-ethyl-6-methylphenyl)acetamide (-acetochlor"), and (RS)-2-chloro-N-(ethoxymethyl)-N-(2-methoxy-1-methylethyl)acetamide (-dimethenamide"); arenecarboxylic acids such as 3,6-dichloro-2-methoxybenzoic acid (-dicamba"); and pyridyloxyacetic acids such as [(4-amino-3,5-dichloro-6-fluoro-2-pyridinyl)oxy]acetic acid (-fluroxypyr").

It is apparent that various modifications may be made in the formulations and application of the compounds of the present invention without departing from the inventive concepts herein, as defined in the claims.

What is claimed is:

1. A compound having the formula

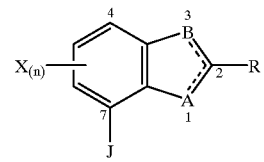

where

A and B are NH;

R is hydrogen, hydroxy, mercapto, straight or branched chain lower alkyl, cycloalkyl, alkoxy, aryl, heteroaryl, alkenyl, haloalkyl, hydroxyalkyl, haloaryl, alkoxyaryl, arylalkyl, aryloxyalkyl, haloarylalkyl, alkylthio, heterocyclyl, alkoxyalkyl, alkoxylalkyloxyalkyl, alkylcarbonyloxyalkyl, arylcarbonyloxyalkyl, aminocarbonyloxyalkyl, aminoalkyl, cyanoalkyl, aminoalkenyl, carboxy, carboxyalkyl, alkylcarboxy, alkylcarboxyalkyl, formyl, aminocarbonyl, amino, oxygen, cyano, nitro, alkylsulfonyl, aminosulfonyl, alkylsulfonylamino, alkylcarboxyoxyalkyl, akylcarboxylalkoxy, alkoxycarbonylamino, alkoxycarbonylalkylaminoalkyl, aryliminoalkyl, (aryl)(alkoxy)alkyl, (aryl)(alkylcarbonyloxy)alkyl, arylalkoxyalkyl, cyanoalkylthio, alkynylalkylthio, arylalkylthio, cyanothio, cyanothioalkyl, alkoxycarbonylalkylthio, aminocarbonylalkylthio, alkenylalkylthio, haloalkylalkynylalkylthio, alkylcarbonylaminoalkyl, arylalkylcarbonylaminoalkyl, (hydroxy)(aryl)alkyl, alkylcarbonylaminoalkyl, alkylsulfonylaminoalkyl, aminocarbonylalkyl, alkoxycarbonyl, and alkenyloxy, where the amino group may be substituted with one or two substituents independently selected from alkyl, hydroxy, alkoxy, carboxy, aryl, alkylsufonyl or haloalkylsulfonyl;

X is hydrogen, F, Cl, Br, alkyl, haloalkyl, CN, $NO_2$, or $NH_2$;

n is 0–3;

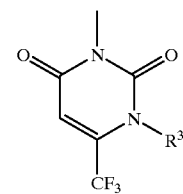

and $R^3$ is hydrogen, alkyl, haloalkyl, $CH_2CN$, $CH_2CH=CH_2$, $CH_2C\equiv CH$, $CH_2CO_2(alkyl)$, $CH_2OCH_3$, or $NH_2$.

2. A herbicidal composition comprising a herbicidally effective amount of a compound of claim 1 and a herbicidally compatible carrier therefor.

3. A herbicidal composition comprising an herbicidally effective amount of a compound of claim 1 and an herbicidally effective amount of one or more herbicides selected from the group consisting of glyphosate, 2,4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, metachlor, acetochlor, dimethenamide, dicamba, and fluroxypyr.

4. The herbicidal composition of claim 3 further comprising a herbicidally compatible carrier therefor.

5. A method of controlling undesired plant growth, comprising application to the locus where the undesired plants are growing or are expected to grow, an herbicidally effective amount of a composition of claim 3.

6. A method of controlling undesired plant growth, comprising application to the locus where the undesired plants are growing or are expected to grow, an herbicidally effective amount of a compound of claim 1.

7. A compound having the formula

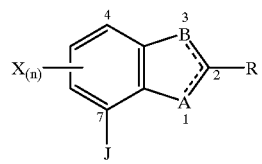

where A is NH and B is nitrogen double-bonded to position 2;

R is hydrogen, hydroxy, mercapto, straight or branched chain lower alkyl, cycloalkyl, alkoxy, aryl, heteroaryl, alkenyl, haloalkyl, hydroxyalkyl, haloaryl, alkoxyaryl, arylalkyl, aryloxyalkyl, haloarylalkyl, alkylthio, heterocyclyl, alkoxyalkyl, alkoxylalkyloxyalkyl, alkylcarbonyloxyalkyl, arylcarbonyloxyalkyl, aminocarbonyloxyalkyl, aminoalkyl, cyanoalkyl, aminoalkenyl, carboxy, carboxyalkyl, alkylcarboxy, alkylcarboxyalkyl, formyl, aminocarbonyl, amino, oxygen, cyano, nitro, alkylsulfonyl, aminosulfonyl, alkylsulfonylamino, alkylcarboxyoxyalkyl, akylcarboxylalkoxy, alkoxycarbonylamino, alkoxycarbonylalkylaminoalkyl, aryliminoalkyl, (aryl)(alkoxy)alkyl, (aryl)(alkylcarbonyloxy)alkyl, arylalkoxyalkyl, cyanoalkylthio, alkynylalkylthio, arylalkylthio, cyanothio, cyanothioalkyl, alkoxycarbonylalkylthio, aminocarbonylalkylthio, alkenylalkylthio, haloalkylalkynylalkylthio, alkylcarbonylaminoalkyl, arylalkylcarbonylaminoalkyl, (hydroxy)(aryl)alkyl, alkylcarbonylaminoalkyl, alkylsulfonylaminoalkyl, aminocarbonylalkyl, alkoxycarbonyl, and alkenyloxy, where the amino group may be substituted with one or two substituents independently selected from alkyl, hydroxy, alkoxy, carboxy, aryl, alkylsufonyl or haloalkylsulfonyl;

X is F, Cl, Br, alkyl, haloalkyl, CN, $NO_2$, or $NH_2$;

n is 2 or 3;

J is

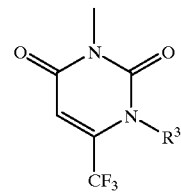

and $R^3$ is hydrogen, alkyl, haloalkyl, $CH_2CN$, $CH_2CH=CH_2$, $CH_2C\equiv CH$, $CH_2CO_2(alkyl)$, $CH_2OCH_3$, or $NH_2$.

8. The compound of claim 1, wherein one X is attached at position 4.

9. The compound of claim 1, wherein R is haloalkyl, X is F or Cl, n is 2, and $R^3$ is alkyl.

10. The compound of claim 9, wherein R is trifluoromethyl, X is F at position 6 and Cl at position 4, and $R^3$ is methyl.

11. A herbicidal composition comprising a herbicidally effective amount of the compound of claim 1 and a herbicidally compatible carrier therefore.

12. A herbicidal composition comprising a herbicidally effective amount of the compound of claim 1 and a herbicidally effective amount of one or more herbicides selected from the group consisting of glyphosate, 2,4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

13. The herbicidal composition of claim 12 further comprising a herbicidally compatible carrier therefor.

14. A method of controlling undesired plant growth, comprising application to the locus where the undesired plants are growing or are expected to grow, a herbicidally effective amount of the composition of claim 12.

15. A method of controlling undesired plant growth, comprising application to the locus where the undesired plants are growing or are expected to grow, a herbicidally effective amount of the compound of claim 12.

16. A herbicidal composition comprising a herbicidally effective amount of the compound of claim 10 and a herbicidally compatible carrier therefore.

17. A herbicidal composition comprising a herbicidally effective amount of the compound of claim 10 and a herbicidally effective amount of one or more herbicides selected from the group consisting of glyphosate, 2,4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

18. The herbicidal composition of claim 17 further comprising a herbicidally compatible carrier therefor.

19. A method of controlling undesired plant growth, comprising application to the locus where the undesired plants are growing or are expected to grow, a herbicidally effective amount of the composition of claim 17.

20. A method of controlling undesired plant growth, comprising application to the locus where the undesired plants are growing or are expected to grow, a herbicidally effective amount of the compound of claim 10.

* * * * *

UNITED STATES PATENT AND TRADEMARK OFFICE
CERTIFICATE OF CORRECTION

PATENT NO.   : 6,077,812
DATED        : June 20, 2000
INVENTOR(S)  : Crawford et al.

It is certified that error appears in the above-identified patent and that said Letters Patent is hereby corrected as shown below:

<u>Claims 8, 9, 11 and 12,</u>
Line 1, delete "1" and insert therefor -- 7 --.

Signed and Sealed this

Ninth Day of April, 2002

Attest:

JAMES E. ROGAN
Attesting Officer          Director of the United States Patent and Trademark Office